(12) United States Patent
Masuda

(10) Patent No.: US 7,624,630 B2
(45) Date of Patent: Dec. 1, 2009

(54) TESTING METHOD AND APPARATUS GROUND LIQUEFACTION AND DYNAMIC CHARACTERISTICS IN ORIGINAL POSITION UTILIZING BORING HOLE

(75) Inventor: Kazuo Masuda, Sagamihara (JP)

(73) Assignee: Masuda Giken Co., Ltd., Shizuoka (JP)

( * ) Notice: Subject to any disclaimer, the term of this patent is extended or adjusted under 35 U.S.C. 154(b) by 257 days.

(21) Appl. No.: 10/583,900

(22) PCT Filed: May 6, 2004

(86) PCT No.: PCT/JP2004/005970

§ 371 (c)(1),
(2), (4) Date: Jun. 21, 2006

(87) PCT Pub. No.: WO2005/066421

PCT Pub. Date: Jul. 21, 2005

(65) Prior Publication Data

US 2007/0144249 A1    Jun. 28, 2007

(30) Foreign Application Priority Data

Dec. 26, 2003   (JP) .............................. 2003-435951

(51) Int. Cl.
*E21B 49/02* (2006.01)
(52) U.S. Cl. ................................................. 73/152.59
(58) Field of Classification Search ............... 73/152.59
See application file for complete search history.

(56) References Cited

U.S. PATENT DOCUMENTS

| | | | |
|---|---|---|---|
| 4,400,970 A * | 8/1983 | Ali | 73/9 |
| 4,554,819 A * | 11/1985 | Ali | 73/9 |
| 4,594,899 A * | 6/1986 | Henke et al. | 73/784 |
| 5,839,317 A * | 11/1998 | Rosenfield | 73/784 |

FOREIGN PATENT DOCUMENTS

| | | |
|---|---|---|
| JP | 54-135407 | 10/1979 |
| JP | 06-173240 | 6/1994 |
| JP | 2002-188137 A1 | 7/2002 |
| JP | 2003-129458 A1 | 5/2003 |

* cited by examiner

*Primary Examiner*—Hezron Williams
*Assistant Examiner*—Rodney T Frank
(74) *Attorney, Agent, or Firm*—Burr & Brown

(57) ABSTRACT

A testing method and apparatus for ground liquefaction and dynamic characteristics in the original position utilizing a boring hole, wherein the dynamic strength and deformation characteristics of a soil layer against a dynamic repetitive load, in an optional position in the ground can be obtained by a simple method. A measuring cell based on a three-chamber construction is used, and upper and lower soil layers (J1, J3) with an intermediate soil layer (J2) therebetween are alternately subjected to a dynamic repetitive load, and what influence there is on the intermediate soil layer (J2) is investigated from the relation between pressure and displacement.

15 Claims, 17 Drawing Sheets

(A)

(B)

(A) 1st step (B) 2nd step (C) 3rd step (D) Kth step (at yielding)

(E) at failure

TESTING METHOD AND APPARATUS GROUND LIQUEFACTION AND DYNAMIC CHARACTERISTICS IN ORIGINAL POSITION UTILIZING BORING HOLE

FIELD OF THE INVENTION

This invention relates to the testing method and apparatus, which are intended to evaluate in-situ the liquefaction and dynamic (strength and deformation) properties of soils using boreholes. Herein, the liquefaction and dynamic properties of soils correspond to those under dynamic cyclic loading such as earthquake loading, traffic loading and machinery vibrations.

BACKGROUND OF THE INVENTION

In the conventional in-situ testing method, a small-diameter bore-hole was produced down to a certain depth from the ground surface, and a cylindrically shaped zonde (inflatable membrane) was lowered down into the bore-hole. The zonde was then inflated and applied the lateral pressure to the surrounding circular wall of the soil deposit, based on the measurements of lateral pressure and radial displacement, the static strength and deformation properties of the soil deposit were inferred.

However, the conventional testing method was intended only to infer the static properties of the soil deposit, and the evaluation of the dynamic properties of the soil deposit, such as those under earthquake loading, traffic loading and machinery vibrations, was out of scope for its use. In the event of earthquakes, however, the strains gradually accumulate locally within the soil deposit leading in some cases to failures, due to the external forces associated with earthquakes, which might be even lower than the collapse loads. It is extremely important therefore to explore the in-situ dynamic properties of soils. The seismic excitations involve complex characteristics and it has not reached a point where the evaluation of the dynamic properties of soils under such complex seismic excitations is properly established.

Among the conventional assessments of liquefaction occurrence, the overall characteristics of the entire ground against liquefaction were examined in some cases. In other cases, the empiricism was used based on past case studies of whether the soil deposit at a particular condition was subjected to liquefaction during past earthquakes or not. In any case, the conventional assessment of liquefaction occurrence was not based on the dynamic properties of the soil deposit itself concerned.

In the current method of evaluating the dynamic properties of a soil deposit under dynamic cyclic loading, undisturbed sampling from a bore-hole and laboratory triaxial tests on undisturbed samples are required. However, it is extremely difficult to perform soil sampling in an undisturbed manner while preserving soil structures in natural deposits during sampling. It is also noteworthy that soil sampling accompanies the stress relief against the overburden stress, since the soil samples are retrieved from the deep soil deposit to the ground surface. It is therefore difficult to precisely evaluate the in-situ properties of the soil deposit in laboratory tests.

In addition, the undisturbed sampling methods for loose sand deposits, gravel-containing soil deposits, soil deposits involving large-sized grains such as sandy gravels, weathered rocks and soft rocks are not well established, and hence it is not practically possible to perform laboratory tests on such soil deposits.

In the current state of practice, it is therefore found that the range of soils that can be supplied to laboratory tests is extremely limited.

SUMMARY OF THE INVENTION

Considering the importance of evaluating in-situ the dynamic properties of the soil deposits, the present invention is intended to offer the comprehensive in-situ testing method and apparatus, which are aimed at exploring the liquefaction and dynamic (strength and deformation) properties of soils using bore-holes, however without difficult undisturbed soil sampling and associated laboratory tests.

In order to achieve the above objectives, the present in-situ testing method is characterized by dynamically excited cyclic loading on the bore-hole wall and monitoring of the lateral pressure and displacement of the bore-hole wall, from which the liquefaction dynamic properties of soils are inferred.

Herein, the dynamically excited cyclic loading constitutes the whole cycles of periodically fluctuating loading, including the wide range of relatively high-frequency loading to low-frequency loading which can be manually operated.

The dynamic properties of soils correspond to those that can be inferred from the relation between the amplitude of the pressure and its associated displacement during dynamically excited cyclic loading, including the yield strength, failure strength, stiffness or shear modulus, and deformation-related properties derived from the pressure amplitude, number of cycles and displacement. The overall dynamic properties of the soil deposit can be evaluated based on those individual dynamic properties of soils.

It is especially effective and found useful to excite laterally the cylindrical wall of a bore-hole in a manner so that the cycles of compressive loading is alternately applied onto the bore-hole wall at multiple locations with depth. By applying the pressures in this manner, it enables us to produce a central region surrounded by the two pressurized regions in a soil deposit, at which the cyclic shear stress parallel to the bore-hole axis acts.

It is at this central region that the soil deposit most approaches a collapse state, and the degree of approaching a collapse state can be estimated based on the static monotonic loading tests on this central region.

More importantly the dynamic properties of soil can be estimated based on the relations among the amplitude of the cyclic pressure, number of cycles and associated displacements during cyclic loading implemented at one or multiple locations with depth.

The cyclic loading is herein represented by the combination of one or more types of loading chosen from compressive loading acting towards the radial direction, torsional loading acting around the bore-hole axis and shear loading acting towards the bore-hole axis.

The in-situ testing apparatus in the present invention is composed of the inflatable membrane zonde which are lowered down into a bore-hole and apply the pressures onto a bore-hole wall via a liquid medium in the zonde, a control unit which can pressurize the liquid medium in the zonde and fluctuate periodically the amplitudes of the pressures in the zonde, and a device which implements the measurement of the displacements of the bore-hole wall.

The zonde is composed of multiple cells located at different positions along the depth, and each cell can be cyclically excited in a manner independent to each other by the control unit. By orchestrating the cycles of the pressures in the multiple cells, it is possible to excite cyclically the bore-hole wall alternately at different positions along the depth.

The control unit applies the cyclic pressures at the top and bottom cells, and applies the constant pressure at the central cell.

The zonde is equipped with a device which generates the torsional cyclic loading around the bore-hole axis while the cells are kept in contact with the bore-hole wall, and also a device which monitors the rotational displacement of the bore-hole wall during torsional cyclic loading.

The zonde is equipped with a device which generates the cyclic shear loading parallel to the bore-hole axis while the cells are kept in contact with the bore-hole wall, and also a device which monitors the shear displacement of the bore-hole wall during cyclic shear loading.

The zonde is composed of multiple cells. The top and bottom cells are those which alternately excite the bore-hole wall cyclically, and the central cell applies the static pressure onto the bore-hole wall. In addition to these three cells, there are two guard cells located above the top cell and beneath the bottom cell, which apply the static pressures.

The zonde is equipped with a device which monitors the pore water pressure at the central cell.

The device for monitoring the pore water pressure possesses a sensor unit on the surface of the inflatable membrane of the central cell.

The zonde is composed of multiple cells, which can be assembled in a manner exchangeable to one another.

Each cell in the zonde is preferably composed of a cell body itself cylindrical inflatable membrane attached to the outer circumference of the cell and a pressure room located between the cell body and the membrane into which a liquid medium is filled.

Seal plates are preferably inserted in between the cells in the zonde, so that the membranes of the adjacent cells can be intimately connected with each other to maintain water-tightness.

The control unit for pressuring the liquid medium in each cell in the zonde is composed of a cylinder which pressurizes the liquid medium and a device which monitors the amplitude (stroke) of the movement of the rod of the cylinder, from which the lateral displacement of the bore-hole wall is obtained.

As described above, the testing method and apparatus in the present invention enable us to perform in-situ testing on natural soil deposits without sampling of soils deep in the deposits, and to evaluate therefore the dynamic properties of natural soil deposits.

This testing method and apparatus can be used to a wide range of soil types, including loose sand deposits and gravel-containing soil deposits which are difficult to perform soil sampling, and also soil deposits involving large-sized grains such as sandy gravels, weathered rocks and soft rocks.

This testing method is also time and cost-saving in comparison to the conventional soil sampling.

This testing apparatus can perform a variety of tests by applying the cyclic pressures alternately to multiple locations along the depth of a bore-hole wall. These kinds of tests are supposed to produce soil elements in the deposit which are either suspected to cyclic compressional stress or subjected to cyclic shear stress at the periphery of the cells. Since soil liquefaction during earthquakes is effectively induced by the action of cyclic shear stress on the soil deposit, this testing method and apparatus are considered useful in the assessment of liquefaction occurrence. When the soil element located at the periphery of the cells is subjected to collapse due to liquefaction, the liquefaction propagates into the region of the soil deposit subjected to compressional stress leading to a rapid change in the displacements of the bore-hole wall.

Another testing method is to perform cyclic loading tests by using only one of the cells in the zonde. From this kind of tests, it is also possible to examine a variety of properties of the soil deposits. In such cases, the cyclic loading can be conducted by the combination of one or more types of loading chosen from compressive loading acting towards the radial direction, torsional loading acting around the bore-hole axis and shear loading acting towards the bore-hole axis.

Since there are two guard cells located above the top cell and beneath the bottom cell, the pressure-displacement relations can also be monitored at these two guard cells. By analyzing these data monitored at the two guard cells in comparison to the data obtained at the central cell, the soil properties can also be examined. In addition, the two guard cells assist in producing a stable condition to perform cyclic loading at the top and bottom cells.

In this testing apparatus which installs the device for pore water pressure measurement at the central cell, it is possible to monitor the change in the pore water pressure at the central cell, which is affected by the cyclic loading imposed on the top and bottom cells adjacent to the central cell.

It is possible to monitor the change in the pore water pressure at the central cell in a direct manner, by installing a sensor unit on the surface of the inflatable membrane of the central cell.

Since the zonde is composed of multiple cells which can be assembled in a manner exchangeable to one another, it is possible to implement maintenance of the zonde such as replacement of parts, on a cell-unit basis.

Since each cell in the zonde is composed of a cell body itself cylindrical inflatable membrane attached to the outer circumference of the cell and a pressure room located between the cell body and the membrane into which a liquid medium is filled, it is possible to implement maintenance of the membrane without difficulty.

This testing apparatus can improve the water-tightness between the membranes of the adjacent cells by inserting the seal plates inserted in between the cells in the zonde. The control unit for pressuring the liquid medium in each cell in the zonde is composed of a cylinder which pressurizes the liquid medium and a device which monitors the amplitude (stroke) of the movement of the rod of the cylinder, from which the lateral displacement of the bore-hole wall is obtained. The water level gauge can be used together to monitor the lateral displacement of the bore-hole wall.

BRIEF DESCRIPTION OF THE DRAWINGS

FIG. 1 (B) shows the general layout of the controlling unit.

FIG. 2 (B) shows an example of typical diagrams illustrating the pressure-displacement relation obtained from the test results using the testing apparatus shown in FIG. 1.

FIG. 11 (B) shows the cross section at the water tube of the top guard cell.

FIG. 11 (C) shows the cross section at the water tube of the top cell.

FIG. 11 (D) shows the cross section showing the layout of the pore water pressure gauge.

DETAILED DESCRIPTION OF THE INVENTION

The mode of the present invention is described in detail below, using schematic examples.

Working Example 1

Figure 1:
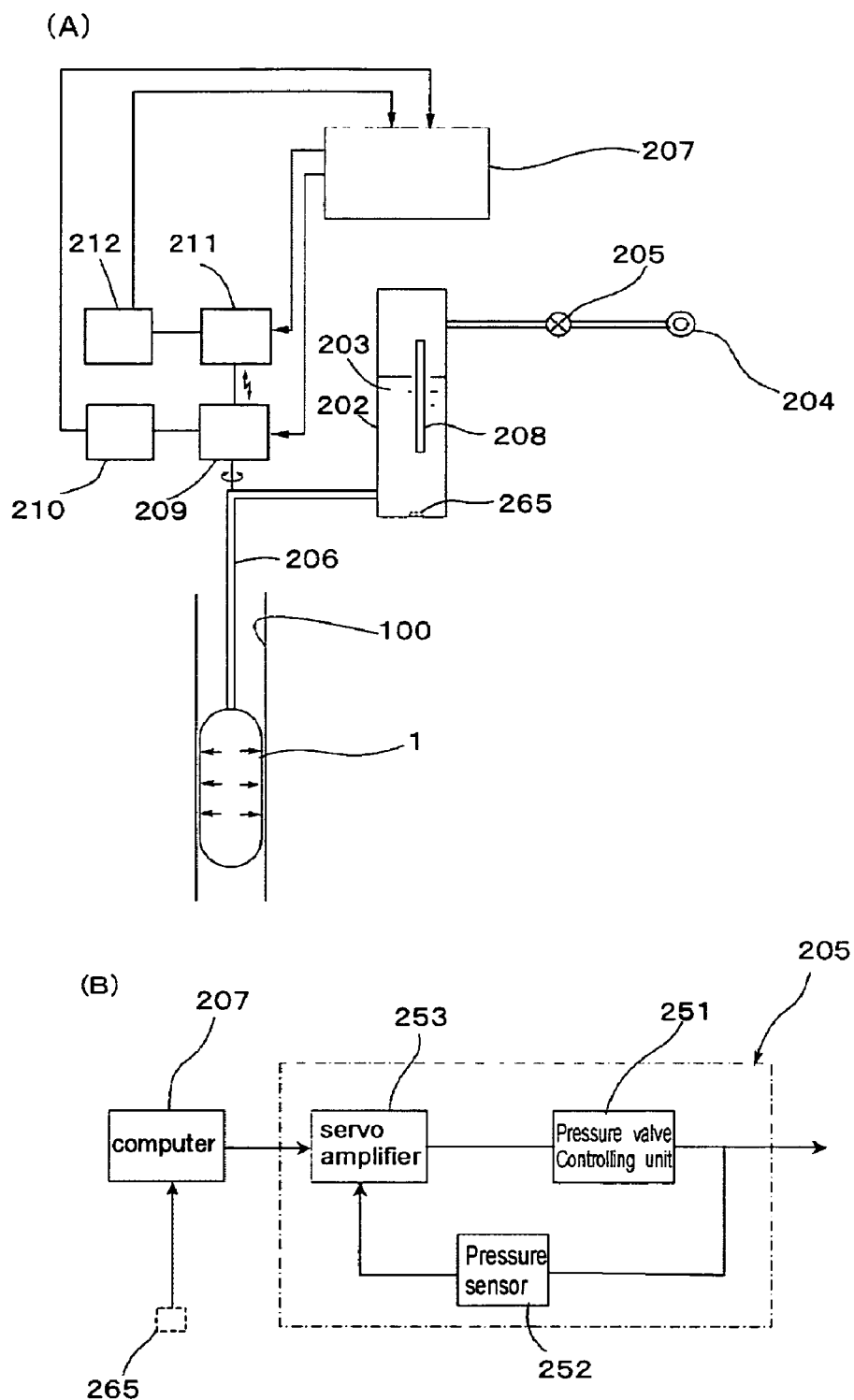
FIG. 1 (A) shows the general layout of the in-situ testing apparatus for liquefaction and dynamic properties of soils using bore-holes, associated with the working example 1.

FIG. 1 (A) shows the schematic illustration of the testing apparatus materializing the working example 1.

This testing apparatus is composed of an inflatable membrane zonde 201, which is lowered down into a bore-hole 100, and apply the pressures onto a bore-hole wall via a liquid medium such as water 203 in the zonde 201, a control unit which can pressurize the liquid medium such as water 203 in the zonde 201, and fluctuate periodically the amplitudes of the pressures in the zonde 201 via a pressure regulator 205, and a device 208 which implements the measurement of the displacements of the bore-hole wall.

In the working example, the water 203 is reserved in the tank 2 on the ground surface. The pressurized air is supplied to a top portion of the water tank 202 from the pressure supplying unit 204. This pressurized air is supplied via the pressure regulator 205 to the water 203 stored in the water tank 202. Instead of regulating the air pressure, the water pressure can be alternatively directly controlled.

The water tank 202 is connected to the inflatable membrane zonde 201 through the connection pipe 206. The displacement sensor 208 monitors the water level in the water tank 202, from which the radial displacement of the bore-hole wall is calculated.

Alternatively, the water level can either be read off directly from the scale attached to the tank 202, or be monitored by the pressure sensor 265 installed at the bottom of the water tank 202.

The inflatable membrane zonde 201 is fixed against the vertical direction, and can be inflated and deflated towards the radial direction. The zonde is composed of hollow cylindrical parts such as a membrane tube which is intimately attached the wall of the bore-hole 100.

The pressure-supplying unit 204 is composed of a gas cylinder of pressurized nitrogen gas and a regulator maintaining the gas pressure supplied from the gas cylinder constant. Air compressors can be alternatively used instead of a gas cylinder.

A servo valve is used as the pressure regulator 205. The pressure supplied through this regulator can be controlled via a voltage signal, as shown in FIG. 1 (B). The voltage signal can be transmitted from the personal computer 207 to the valve-driving unit 51 of the regulator 205 in order to produce cyclically alternating pressures at a given frequency. The amplitude of the pressure is monitored by the sensor 252, and is transmitted back as a feedback to the servo amplifier 253 and the signal is adjusted to make precise control of the pressure change in the system.

The testing procedure for this testing apparatus is described below.

Several base pressure levels are first set up based on the expected levels of yield strength or failure strength (Pl). At each base pressure level beginning from the lowest base level, the cyclically changing pressure is additionally applied and the displacement of the surrounding soil is monitored. The same procedure is repeated at each base pressure level, and the base pressure level is gradually increased until the collapse limit stress is achieved. The dynamic properties of soils are inferred from the pressure-displacement relations at several base pressure levels. In the working example, the sinusoidal cycles of pressures are adopted. However, any form of cycles can be applied, and it is possible to apply impact loading.

The frequency of the cyclic pressure and its number of cycles can be determined based on the characteristics of earthquakes concerned. However, it is preferable to set it at around 0.1 to 1 Hz.

In the working example, the yield strength Py, failure strength Pl and deformation modulus are inferred as representative dynamic properties of soils.

The testing procedure is described in detail from the practical point of view below.

i) Setting Up Test Series

The inflatable membrane zonde 201 is lowered down to a given soil layer in a bore-hole 100. The zonde 201 is then inflated until the membrane is intimately attached to the bore-hole wall, at which point the change in the displacement stabilizes, and the level of the pressure at such point is determined as the initial stress level Po.

The expected level of the failure strength or limiting stress is first determined. A series of tests are supposed to be conducted at different base pressure levels. The number of tests N is decided, and the level of the base pressure at each test is determined based on the equal increment of the base pressure level, $\Delta P=(Pl-Po)/N$. The cyclic loading is applied for n cycles or for the time period of Tn at each base pressure level.

The expected level of the failure strength or limiting stress can be set up arbitrarily based on the objectives of the tests. For instance, the level of the limiting stress can be set up at a high value so that the number of tests can be increased. The limiting stress corresponds to the level of the pressure below which the occurrence of soil liquefaction is less likely and can be determine based primarily on the conditions of the soil layer concerned.

The number of cycles and time duration of cyclic loading can be set up arbitrarily and for instance can be determined by considering the characteristics of earthquakes concerned. In the working example, 10 levels of the base pressures are set up, and the cyclic loading are applied for 20 cycles or 120 seconds at each base pressure level. Herein, the duration of 120 seconds is considered as appropriate, since the duration of earthquakes is in most cases less than 120 seconds, and it becomes time consuming if the duration becomes longer.

ii) 1st Base Pressure Level

The cyclic loading with amplitudes varying between Po and Po+$\alpha$ is applied for 20 cycles or 120 seconds, and the displacement is monitored during the cyclic loading. The Parameter $\alpha$ should take a value that does not exceed $\Delta P$ or is preferably equal to $\Delta P$.

iii) kst Base Pressure Level

The same procedure is repeated at each base pressure level.

For instance, at the kst base pressure level, the level of the base pressure Pk is increased up to Po+(k−1)$\Delta P$. The cyclic loading with amplitudes varying between Pk and Pk+$\alpha$ is applied for 20 cycles or 120 seconds, and the displacement is monitored during the cyclic loading.

Figure 2:
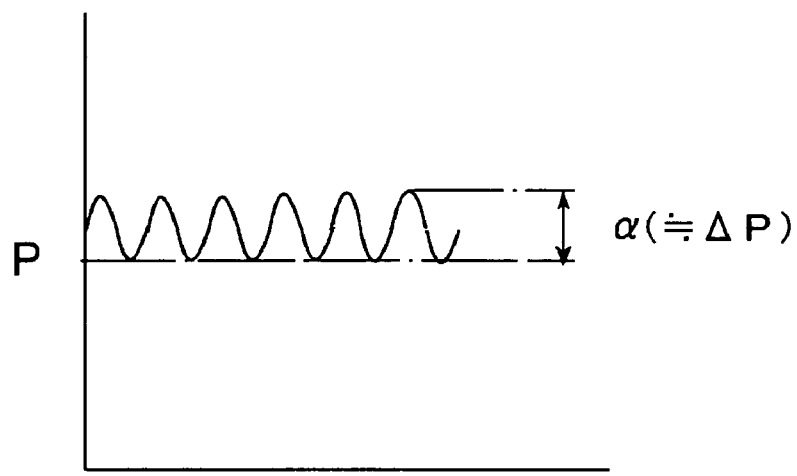
FIG. 2 (A) shows an example of output from the pressure valve shown in FIG. 1.
Figure 2:
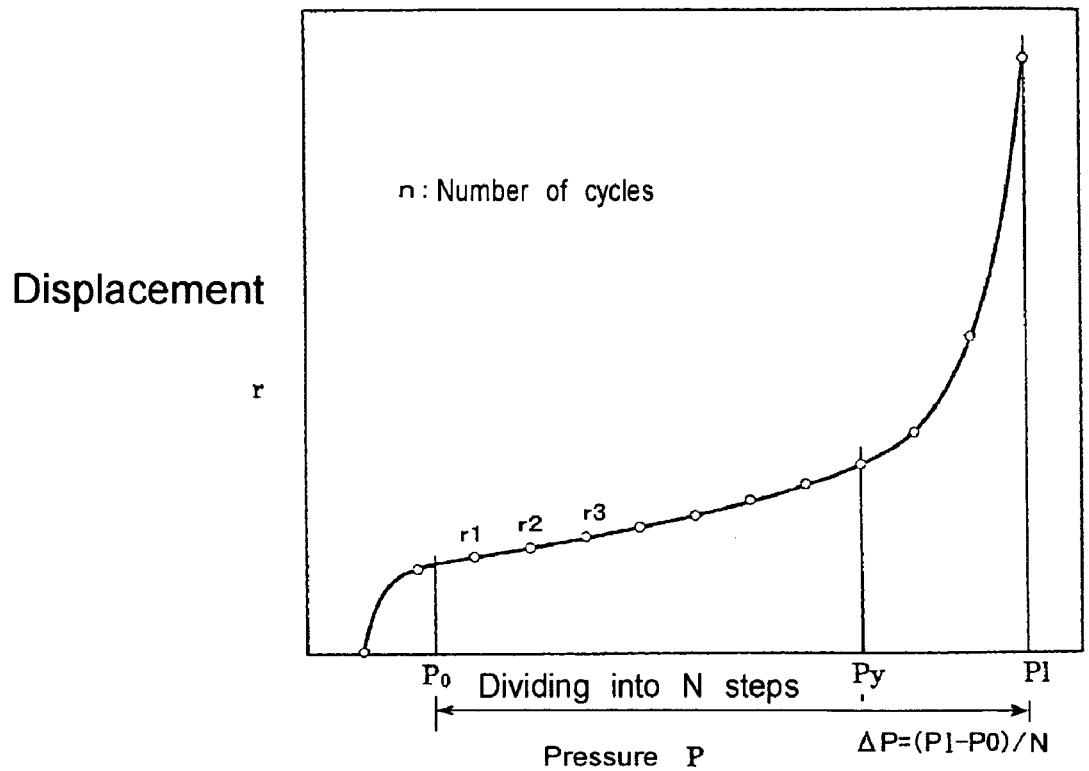

The data thus obtained from the tests are translated in to a diagram as shown in FIG. 2 (B). In this diagram, the final level of the displacement at each base pressure level is indicated as r1, r2, r3 and so forth.

In the working example, the voltage outputs acquired from the pressure sensors are converted into digital data and saved in the personal computer. The data thus obtained are automatically calibrated to infer the yield strength Py, failure strength Pl and deformation modulus. The deformation modulus herein corresponds to the gradient of the initial linear portion of the pressure-displacement relation.

By systematically analyzing the data of the displacements increasing with the number of cycles, the strength and deformation characteristics of soil deposits can be examined.

In other words, it becomes possible to evaluate the possibility of liquefaction occurrence based on the comparisons with other geotechnical test results.

In the case of sandy soil deposits, the state of failure is expected to occur rapidly and the relation of the pressure-displacement is also expected to reach the state of failure rapidly. By examining the degree of such a rapid change leading to a failure state, it is possible to examine the level of damages induced by liquefaction.

In the case of clayey soil deposits, the state of failure is expected to occur rather slowly. By examining the degree of such as low change, it is possible to examine the dynamic characteristics of soils.

Overall, by examining the process of development of displacements leading to a failure state during cyclic loading, the degree of strength reduction can be estimated regardless of soil types.

iv) Important Items During Monitoring

Proper attention should be given to the process of development of displacements, and the point of time at which the displacements begin to rapidly increase needs to be recorded. The data acquisition might be terminated at such a point of time by interpreting it as being equivalent to a state of yielding. Otherwise, the data acquisition can be extended until the state of failure is clearly seen.

The pressure in the membrane zonde 201 is reduced down below Po, and the zonde is then pulled up to the ground surface proper attention is given to the resistance of soil during the lift-up of the zonde. When the lift-up of the zonde is found to be difficult, the bore-hole wall is most probably collapsed due to liquefaction induced during testing.

Figure 3:
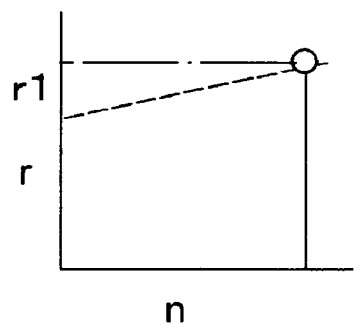
FIG. 3 shows other associated diagrams of the test results using the testing apparatus shown in FIG. 1.
Figure 3:
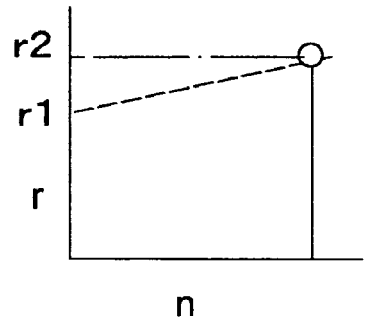
Figure 3:
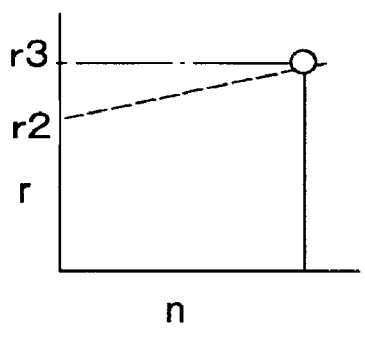
Figure 3:
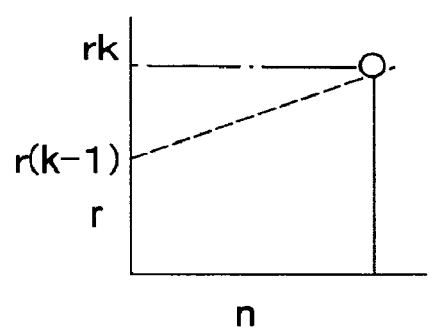
Figure 3:
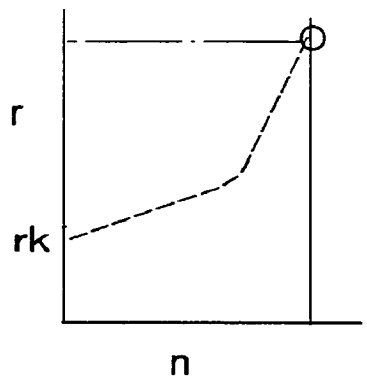

In the working example, the relation between the pressure and displacement is translated in a diagram. However, as shown in FIGS. 3 (A) to (D), the relation between the displacement and number of cycles at each base pressure level can be translated into a diagram, and it is possible to examine the dynamic properties of soil with regard to the number of cycles. In these diagrams, the peak value of the displacement at each cycle is plotted against the number of cycles. This plot is produced at each base pressure level. It is certain that the displacements gradually accumulate during cyclic loading. It is seen that in the 1st, 2nd and 3rd cycles shown in FIGS. 3 (A) to (C), the gradients of the displacement accumulation are the same, and the gradient becomes larger at the state of yielding, (FIG. 3 (D)), and eventually the gradient becomes extremely large at the state of failure as shown in FIG. 3 (E). By obtaining this kind of data, it is possible to examine the dynamic strength and deformation characteristics of soils against cyclic loading.

Alternatively it is possible to plot the displacements against the period of time of cyclic loading, and it is recommended to examine various types of soil properties.

In the working example 1, the cyclic loading acting towards the radial direction is adopted.

However, it is also possible to adopt other types of cyclic loading such as torsional loading acting around the bore-hole axis, and shear loading acting parallel to the bore-hole axis.

For instance, in the case of torsional cyclic loading, the following units need to be installed, i.e. the monitoring zonde 201 which would be intimately attached to a bore-hole wall during its operation, the driving unit 209 for torsional loading generated around the bore-hole axis, and the monitoring unit 210 for the rotational displacements of the bore-hole wall during torsional loading.

In the case of cyclic shear loading, the following units need to be installed, i.e. the monitoring zonde 201 which would be intimately attached to a bore-hole wall during its operation, the driving unit 211 for shear loading generated parallel to the bore-hole axis, and the monitoring unit 212 for the shear (axial) displacements of the bore-hole wall during shear loading.

The driving unit 209 for torsional loading and the driving unit 211 for shear loading can be made up of various types of devices. However, it is preferable to use hydraulic driving units employing the oil pressure or air pressure, and the combinations of hydraulic actuators and relevant regulators such as a servo-valve can be used.

Working Example 2

The working example 2 is described below.

Figure 7:
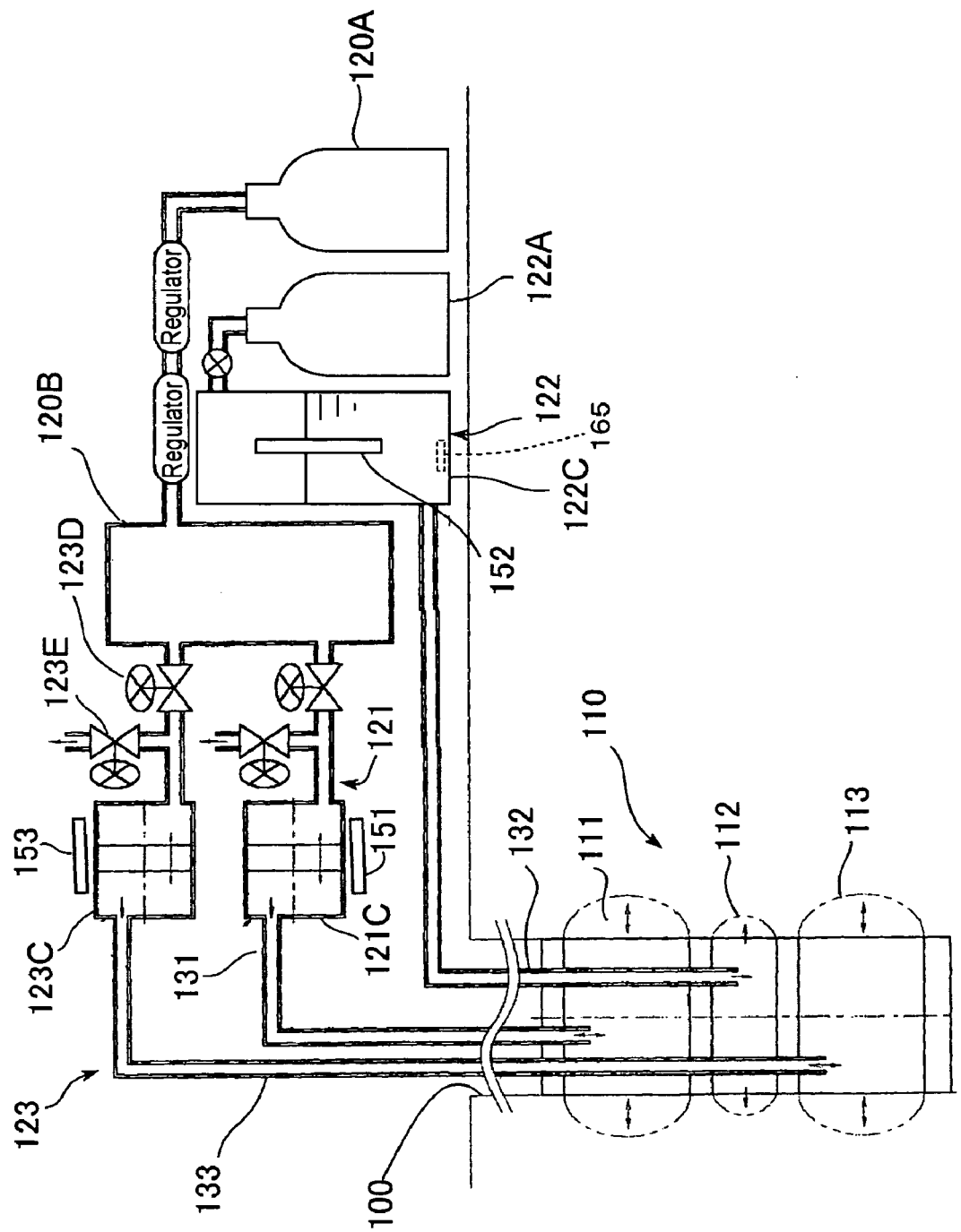
FIG. 7 shows the general layout of the in-situ testing apparatus for liquefaction and dynamic properties of soils using bore-holes, associated with the working example 2.

FIG. 7 shows the general layout of the in-situ testing apparatus in the present invention, which is aimed at exploring the dynamic properties of soils using bore-holes.

In the working example 1 described above, the cyclic loading is employed only on one location with a single cell of the zonde. However, in the working example 2, the cyclic loading is alternatively imposed on the top and bottom parts of the soil layer, J1 and J3, in such a manner that the soil element at the central part, J2, is subjected to cyclic shear stress.

Herein, the membrane zonde 110, which is lowered down into a bore-hole 100, is composed of three independent cells, 1st cell 111, 2nd cell 112 and 3rd cell 113, which are filled with a liquid medium. The 1st cell 111 and 3rd cell 113 are alternatively cyclically excited by the 1st controlling device 121 and the 3rd controlling device 123, while the 2nd cell is statically pressurized by the 2nd controlling device 122.

Figure 5:
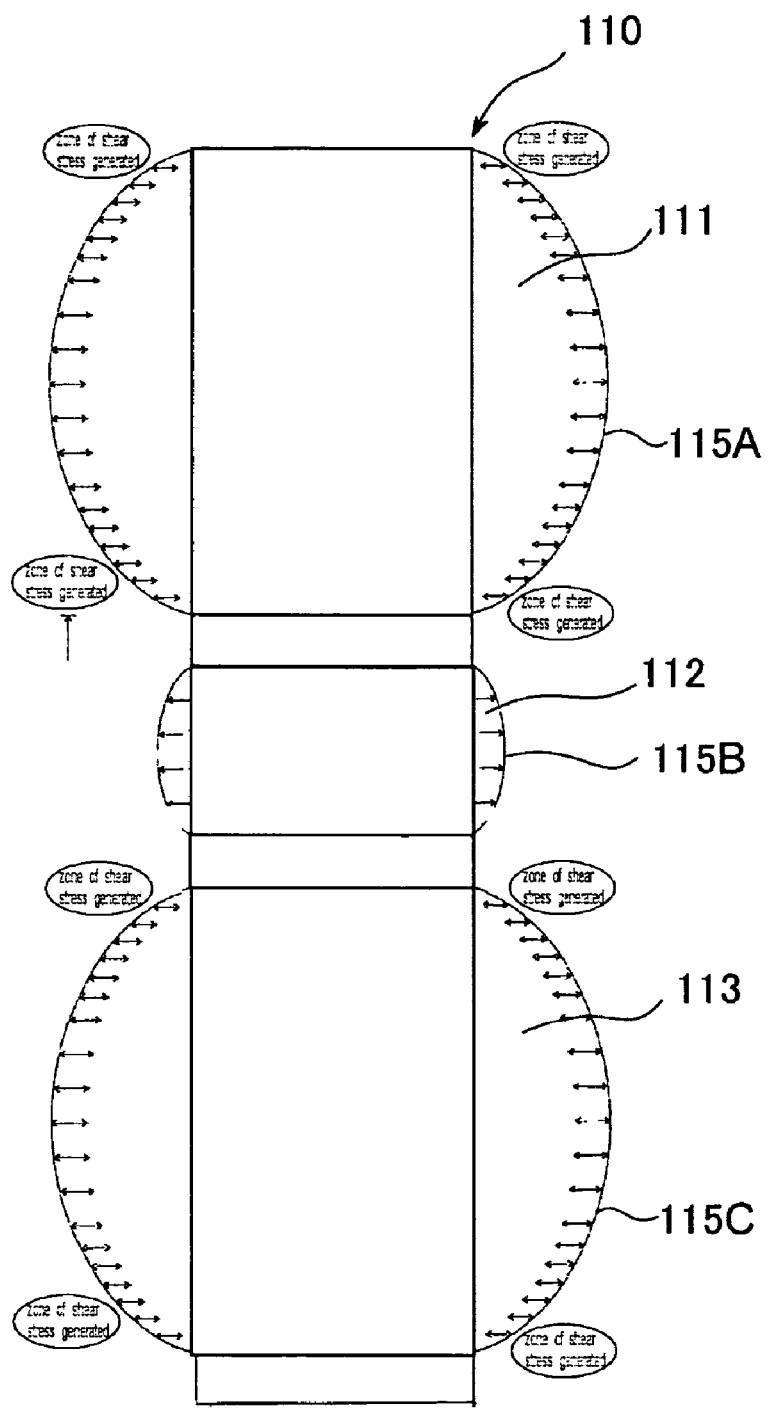
FIG. 5 shows the functions of the membrane zonde shown in FIG. 4.
Figure 6:
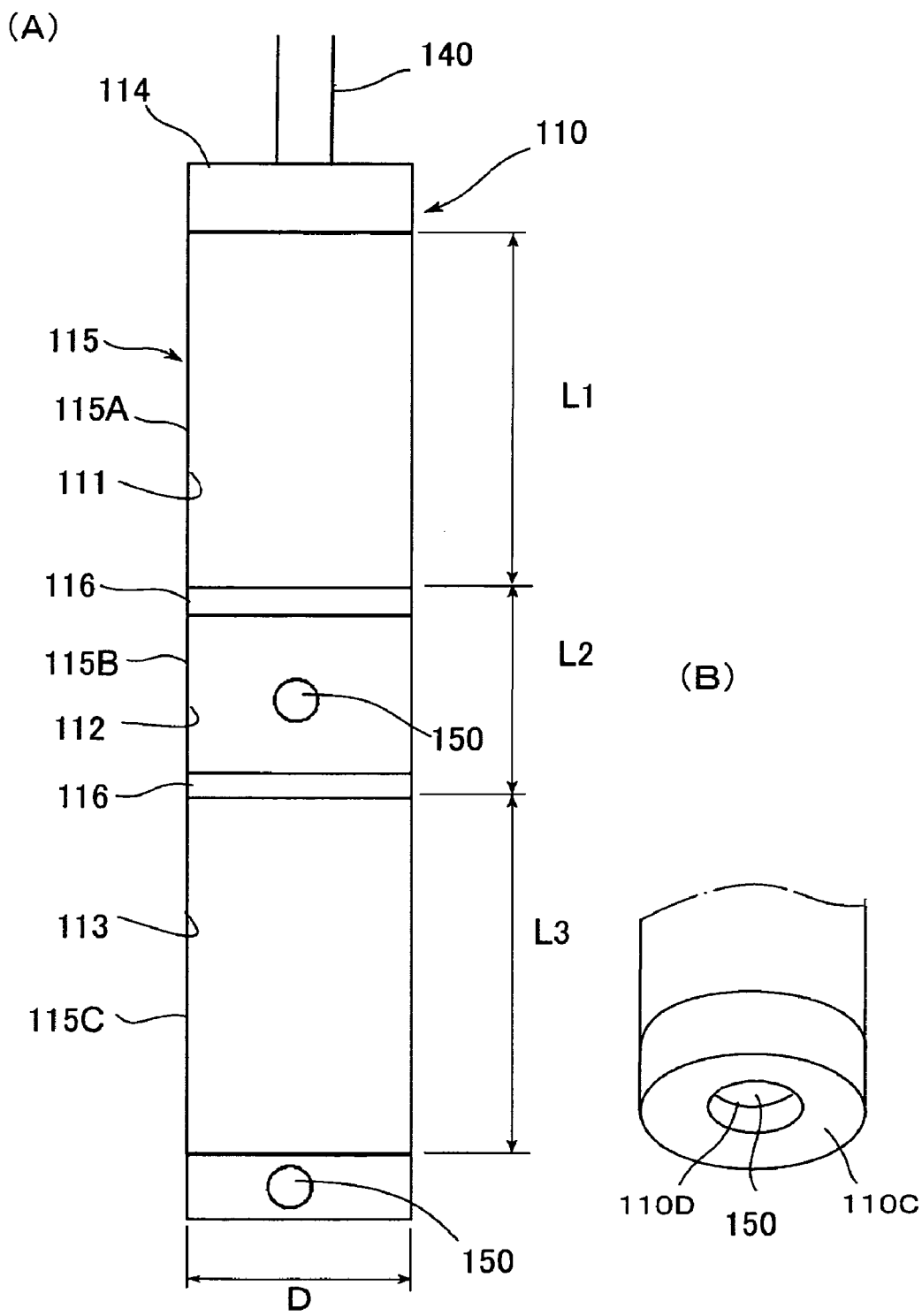
FIG. 6 shows the general layout of the membrane zonde shown in FIG. 5.

The membrane zonde 110 is composed of a cylindrical cell body 114 itself and a cylindrical membrane 115 which is attached to the outer circumference of the cell body as shown in FIGS. 5 and 6. The cylindrical membrane 115 covers all of the three cells, i.e. the 1st cell 111 and 2nd cell 112, and 3rd cell 113. The seal plates can be attached between the 1st cell 111 and 2nd cell 112, and also between the 2nd cell 112 and 3rd cell 113, or these seal plates can be attached to each cell. Various types of cell structures are possible. In what follows, the membranes for the 1st cell 111, 2nd cell 112 and 3rd cell are called 115A, 115B and 115C. The zonde is therefore composed of the 1st cell 111, 2nd cell 112 and 3rd cell 113 and the corresponding membranes 115A, 115B and 115C.

It is preferable to make the length of the central (2nd) cell (or membrane 115B), L2, equal to about the diameter of the zonde 110. This is because of the fact that the failure of soils adjacent the central (2nd) cell would commence earlier in the tests if the length of the 2nd cell (membrane 115B), L2, is small, while the failure of soils adjacent to the central (2nd) cell would not occur if the length, L2, is large.

The length of the 1st cell 111 and 3rd cell 113 (membranes 115A and 115C) is better taken as 1.5 to 2.5 times the diameter of the zonde, D, and is preferably 2 times the diameter of the zonde, D. Herein, the diameter of the zonde, D, is preferably taken as 5 cm to 20 cm. However, it is not intended to limit any use of other sizes of equipments. These recommended sizes would enable the membranes 115A and 115C, which are attached to the 1st cell 111 and 3rd cell 113, to inflate in a spherical manner, and also would enable the soil element J2 located adjacent to the central cell to be subjected to cyclically alternating shear stress.

As shown in FIG. 7, the 1st and 3rd pressure controlling devices, 121 and 123, are composed of a gas cylinder 120A, which supplies high pressures to the system, a gas tank 120B, which reserves an amount of gas supplied from the gas cylinder 120A, and hydraulically operated cylinders, 121C and 123C, which are activated by the hydraulic pressures supplied from the gas tank 120B. Installed between the gas tank 120B and the cylinders of 121C and 123C are the valves of 121E and 123E, which would release the pressures, and also the valves of 121D and 123D, which would supply the pressures. By adjusting these valves of 121D, 121E, 123D and 123E, the 1st cell 111 and 3rd cell 113 in the zonde 110 can be cyclically excited.

For instance, the valves of 121D and 123D can be used as pressure regulators, while the valves of 121E and 123E are closed. By adjusting the gas pressures supplied into the cylinders of 121C and 123C by means of the valves of 121D and 123D, the 1st cell 111 and 3rd cell 113 can be activated. The valves of 121D and 123D are indicated in FIG. 6 with a symbol of manual valves, however, they can be replaced by other types of valves such as electrically operated regulators. After the testing, the gas pressures in the cylinders of 121C and 123C should be released by opening up the valves of 121E and 123E. In this example, water is used as a liquid medium in the system, and the membranes 115A and 15C are inflated and deflated by the water pressure.

The hydraulically operated cylinder is not installed for the 2nd pressure controlling device.

Instead, the water 3 is reserved in a water tank 122C, and the empty top portion of the water tank 122C is pressurized by supplying the gas pressure from the gas cylinder 122A. This gas pressure is controlled by the regulator 122D. It is possible to use the same cylinder as those of the 1st and 3rd pressure controlling devices, 121 and 123.

The cylinder 121C and the 1st cell 111 in the zonde 110 are connected by the 1st line 131, and the water tank 120C and the 2nd cell are connected by the 2nd line 132, and the cylinder 123C and the 3rd cell 113 are connected by the 3rd line 133. These three lines of 131, 132 and 133 are installed along the boring rod 140 to which the zonde is fixed.

The displacement sensors, 151 and 152, are installed at the cylinders of 121C and 123D.

These displacement sensors are used for monitoring the radial displacements of the top soil layer J1 and the bottom soil layer J3, which are cyclically loaded by the 1st cell 111 and 3rd cell 113.

The displacements of the pistons of the cylinders thus monitored are calibrated into the radial displacements of the membranes of 115A and 115C in the zonde 110, which are equivalent to the radial displacements of the bore-hole wall.

The displacement sensor 153 is installed to monitor the water level in the water tank 122C, from which the radial displacement of the bore-hole wall at the soil layer J2 adjacent to the central (2nd) cell 112 in the zonde 110 is calibrated. From the water level thus monitored, the radial displacements of the membrane 115B attached to the 2nd cell 112, and therefore of the bore-hole wall are obtained. Instead of using the displacement sensor 153, the radial displacement of the bore-hole wall can either be obtained by the scale attached to the tank 122C, or be monitored by the pressure sensor 165 installed at the bottom of the water tank 122C. In addition, at the bottom of the membrane zonde 110 installed is the pore pressure transducer 150 for examining the occurrence of liquefaction. This pore pressure transducer 150 can be installed either at the center or at the bottom of the side wall of the membrane 115B of the 2nd cell 112, as shown in FIG. 6 (A). Since there is a possibility that the pore pressure cannot be measured due to clogging at the bore-hole wall, the pore pressure transducer can be installed at the bottom surface 110C as shown in FIG. 6 (B). However, when the zonde 110 is lowered down into a bore-hole 100, the remnants of soils scraped by the zonde 110 may be adhered to the bottom surface 110C. Therefore, it is preferable to install the transducer deep in the concave part of the bottom surface 110D.

Figure 4:
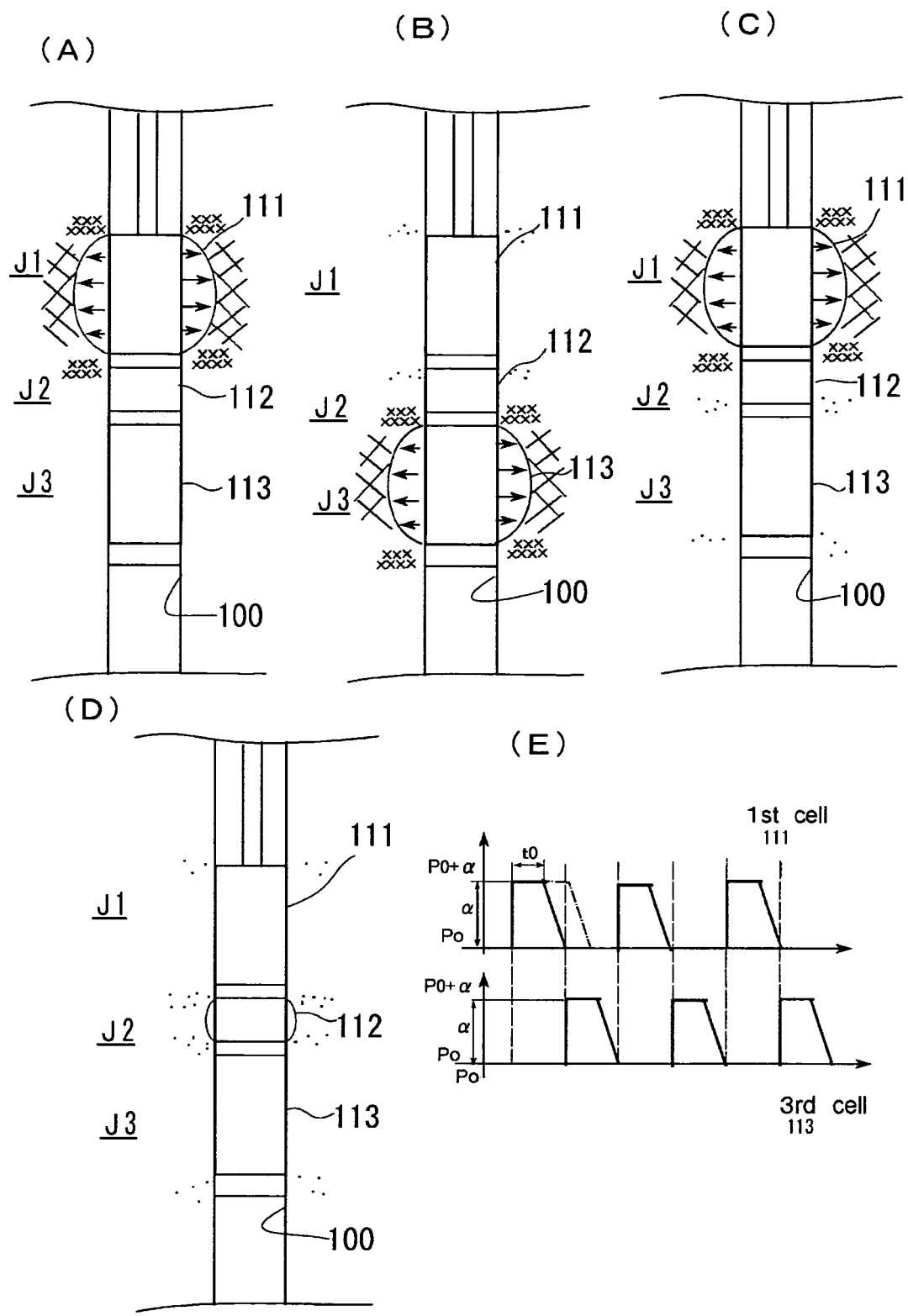
FIGS. 4 (A) to (E) show the testing method using the in-situ testing apparatus for liquefaction and dynamic properties of soils using bore-holes, associated with the working example 2.

The testing procedure for the working example 2 is described below, with reference to FIG. 4.

In the tests, the cyclic loading is applied to the top and bottom soil layers J1 and J3, alternatively and the associated displacements are monitored on a real-time basis. The static loading is then applied to the central soil layer J2 to derive the static strength of soils.

The manner in which the cyclic loading is applied to the top and bottom soil layers, J1 and J3, is the same as that adopted in the working example 1. By dividing the expected level of the yield strength or limiting stress (Pl) by the number of tests N, the level of the base pressure at each test is determined. The cyclic loading whose amplitude is set at $\alpha$ is applied for n cycles or for the time period of Tn at each base pressure level. By monitoring the displacements r, the static strength of the central soil layer J2 is derived at each level of the base pressure.

The testing procedure is described in detail from the practical point of view below.

The bore-hole 100 is produced down to a depth of testing, and the membrane zoned lowered down into the bore-hole 100 with a help of the boring rod 140. The tests commence following the procedure as described below.

i) Setting Up Test Series

By supplying the pressure to the 2nd cell 112 in the zonde 110, the static loading is applied to the central soil layer J2 and the initial strength of the central soil layer J2 is derived. In other words, the relation between the pressure P and the displacement r under static loading is obtained.

At this point of time, the initial pressure Po is obtained, which corresponds to the state at which the membrane zonde is intimately adhered to the bore-hole wall and the displacement is stabilized.

The expected level of the failure strength or limiting stress (Pl) is first determined. The number of tests N is decided, and the level of the base pressure at each test is determined based on the equal increment of the base pressure level, $\Delta P = (Pl - Po)/N$. The cyclic loading is applied alternatively to the 1st cell 111 and 3rd cell 113 for n cycles or for the time period of Tn at each base pressure level. Prior to the cyclic loading, the initial pressure Po is applied to the 1st cell 111 and 3rd cell 113.

ii) 1st Base Pressure Level

The cyclic loading with amplitudes varying between P0 and Po+α is applied alternatively to the 1st cell 111 and 3rd cell 113 for n cycles, and the displacements of the top and bottom soil layers J1 and J3 corresponding to the 1st cell 111 and 3rd cell 113 are monitored. The relations between the pressures and displacements are monitored on a real-time basis in a manner similar to the working example 1 and the acquired data are stored in the personal computer and are translated into a diagram. In this case, the number of tests may be taken at about N=10, and the cyclic loading may be applied for about 20 cycles or for 120 seconds. In this case, the rapidly growing impact loading is applied as shown in FIG. 4 (E). The soil layer is steadily compressionally loaded, while the level of the loading is kept for a time period until after the impact loading stops rapid growing. The level of loading then steadily reduces. The loading is applied alternatively to the 1st cell 111 and 3rd cell 113, in a manner that one of the cells is loaded while the other one is unloaded. The time history of loading is designed in such a manner that the level of loading begins to reduce in one of the cells, after which point of time the level of loading begins to increase in the other cell. However, these two characteristic points of time may be designed to coincide with one another, as shown in dashed lines.

The upper portions and lower portions of the top soil layer J1 and the bottom soil layer J3 are subjected to compressional as well as shear loading. Especially at the central soil layer J2, the cyclically alternating shear loading is applied in a manner similar to the action during earthquakes, since the cyclic loading alternatively applied on the top and bottom soil layers, J1 and J3, as shown with the symbols of X in FIGS. 4 (A) to (C). The length of the 2nd cell 112, L2, is designed to be almost equal to the diameter of the membrane zonde 110, and the phenomena leading to failure are observed adequately.

Since the lengths of the 1st cell and 3rd cell, L1 and L3, are about twice the diameter D, the membranes 115A and 115C are supposed to inflate in a spherical shape, and consequently the compressional loading thus generated is distributed around the central soil layer J2. Therefore, the size of the equipment is designed to make effective use of effects of loading on the soil layer.

iii) After Cyclic Loading

The pressure is again supplied to the 2nd cell 112, and the static loading is applied to the central soil layer J2. The strength of the soil at the central layer J2 is thus measured, and the strength reduction is evaluated relative to the initial strength.

The above procedure is taken as one cycle, and the cyclic loading is repeated with the pressure increment of DB until the failure of the soil layer is observed.

Figure 8:
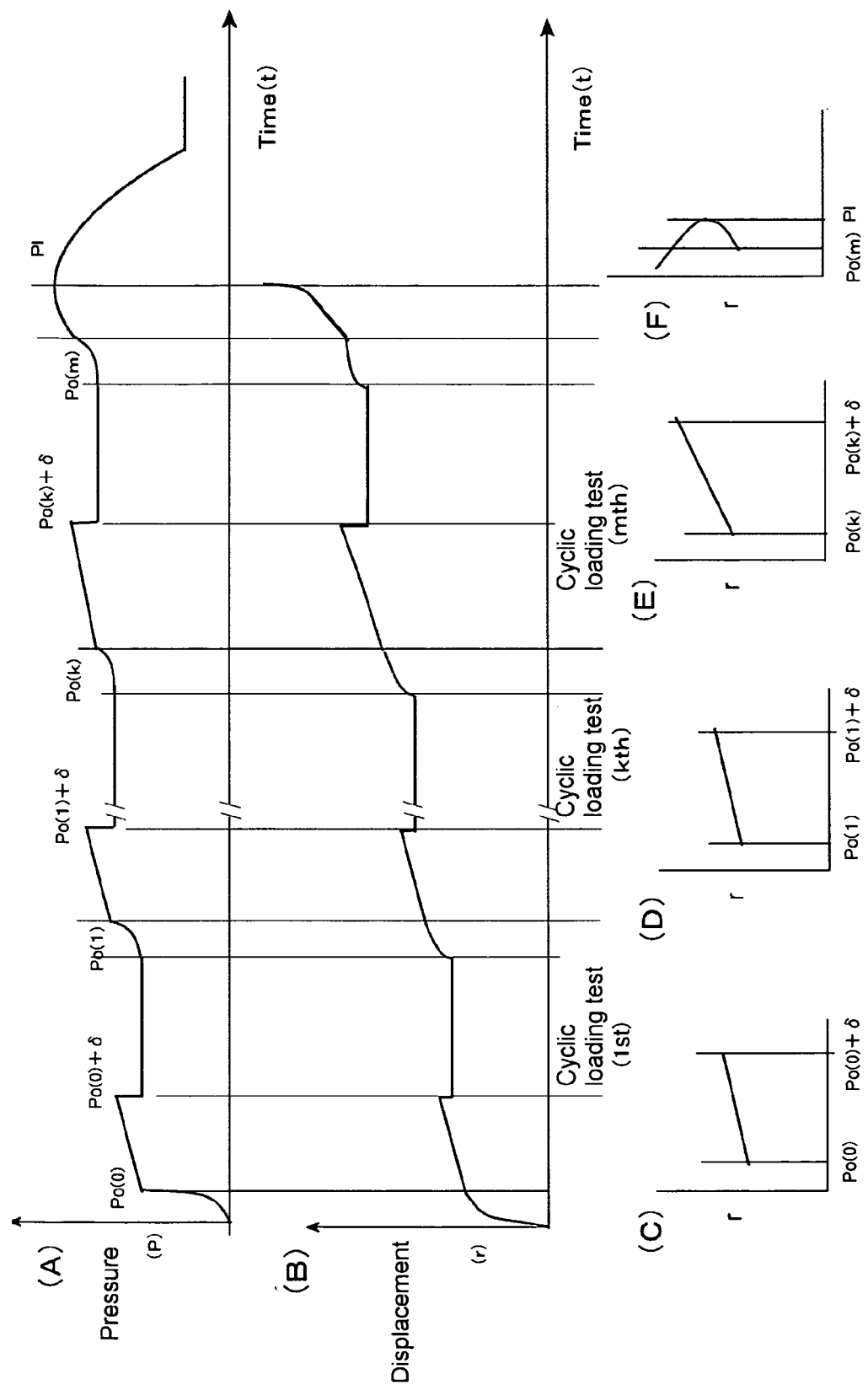
FIGS. 8 (A) to (F) show examples of diagrams illustrating the static test results conducted on the central soil layer.

FIG. 8 shows the example of the results of the static loading tests conducted at the central soil layer J2.

The static pressure P at the central soil layer J2 is plotted against time in FIG. 8 (A), and the corresponding displacement r at the central soil layer J2 is plotted against time in FIG. 8 (B). In FIGS. 8 (C) to 8 (F), the relation between the pressure and the displacement at the central soil layer J2 at each base pressure level is plotted based on the data shown in FIGS. 8 (A) and (B).

As shown in FIGS. 8 (A) and 8 (B), the initial strength of the central soil layer is measured prior to the cyclic loading.

The displacement steadily increases without the increase in the pressure, until the membrane 115B of the 2nd cell 112 in the zonde 110 is intimately adhered to the bore-hole wall 100. Once the membrane is adhered to the bore-hole wall, the pressure rapidly begins to increase with little change in the displacement, and the pressure eventually reaches the initial pressure Po with the change in the displacement stabilized. After that, the displacement is monitored during the increase in the pressure up to Po+δ, and the relation between the pressure and the displacement of the central soil layer at the initial base pressure level is produced, as shown in FIG. 8 (C). The gradient of this pressure-displacement relation is defined as the deformation modulus. The pressure is then reduced down to Po (0). Although the pressure is reduced down to the original level of Po, the residual displacement remains at the central soil layer, and therefore the displacement would not recover completely. The pressure increment δ is determined as a half, one-third, or one-fourth of the amplitude of the cyclic loading imposed on the top and bottom soil layers, J1 and J3. Herein, the least necessary is the pressure-displacement relation which can be comprehensively analyzed without difficulty.

The static loading is then conducted at the central soil layer J2, after the first cyclic loading on the top and bottom soil layers, J1 and J3.

The displacement steadily increases without the increase in the pressure, until the membrane 115B is inflated to the level of the residual displacement at the first base pressure level. Once the level of residual displacement is reached, the pressure rapidly begins to increase with little change in the displacement, and the pressure eventually reaches the previously experienced pressure Po (1). After that, the displacement is monitored during the increase in the pressure up to Po (1)+δ, and the relation between the pressure and the displacement of the central soil layer at the second base pressure level is produced, as shown in FIG. 8 (D). The gradient of this pressure-displacement relation is again defined as the deformation modulus. The pressure is then reduced down to Po (1). Although the pressure is reduced down to the level of Po (1), the residual displacement remains at the central soil layer J2, and therefore the displacement would not recover completely.

In a manner similar to the above, the static loading is conducted at the central soil layer J2, after the cyclic loading on the top and bottom soil layers, J1 and J3. As long as the recoverable elastic zone is concerned, the deformation modulus obtained from the pressure-displacement relations remains almost the same.

After a few tests of cyclic loading (kth), the central soil layer J2 experiences the state of yielding. In such a case, it takes time to increase the level of the pressure from Po (k) to Po (k)+δ, and at the same time the displacement steadily increases with little change in the pressure. The relations between the pressures and the displacements in such cases become steeper, as shown in FIG. 8 (E).

Eventually, the central soil layer J2 experiences the state of failure, (at the mth test corresponding to the next test after the state of yielding is reached). The pressure is then reduced after achieving the peak P1 and becomes stable when the pressure reduces down to a certain level of pressures such as a hydro-static pore water pressure. The displacement begins to increase rapidly at around the state of failure as shown in FIG. 8 (B), and the pressure-displacement relation shows a curve in which the displacement increases while the pressure even decreases.

By examining the data of the displacements at the top and bottom soil layers, J1 and J3, during cyclic loading, and the data of the displacement at the central soil layer J2 during static loading, the dynamic deformation characteristics of soils can be examined, and the yield strength and the failure strength are derived.

Liquefaction is supposed to occur at the central soil layer J2, where the cyclic shear stress acts from both of the top and bottom layers Once the liquefaction is induced, the displacement in the data shown in FIG. 8 begins to increase rapidly and the occurrence of liquefaction can be confirmed. The occurrence of liquefaction can also be confirmed by observing whether the pore water pressure becomes stably constant.

As described above in the working example 2, the simple, reliable, time-saving, cost-effective and accurate dynamic testing can be performed by cyclically exciting the top and bottom soil layers alternatively leading to the central soil layer subjected to cyclic shear stress, without resorting to the torsional loading and shear loading parallel to the bore-hole axis as adopted in the working example 1.

In the working example 2, the zone where only the static loading act was provided along the zonde. However, it is also possible to make the zonde formed only by the zones (cells) where the cyclic loading acts, without providing the zone (cell) where the static loading acts, and to pay attention only to the displacements at the top and bottom soil layers. By doing so, the shear loading acts at the boundaries between the top and bottom soil layers, and the effects induced by liquefaction are supposed to propagate to the top and bottom soil layers.

In the working examples described so far, the cyclic loading is applied at the two cells to the top and bottom soil layers. However, it is also possible to provide more than 3 cells at which the cyclic loading is applied. In such cases, the zone of static loading can be provided at the center of the adjacent two zones of cyclic loading.

As far as the manner in which the cyclic loading is applied is concerned, it can be applied either as compressional loading acting towards the radial direction against the bore-hole axis, or as torsional loading acting around the bore-hole axis, or as shear loading acting parallel to the bore-hole axis. It can be applied as combinations of the types of loading described above.

In the working examples 1 and 2, the bore-hole 100 was produced orthogonal to the ground surface. However, it can be produced in the directions parallel to the ground surface, or in the directions oblique to the ground surface.

Instead of using the membrane zondes 110 and 111 as monitoring cells, hydraulically operated metal plates such as piston jacks can also be used. The types of loading devices can be chosen based on the types of soil layers tested.

Working Example 3

The working example 3 for the test apparatus aimed at exploring in-situ the liquefaction and dynamic characteristics of soils using bore-hole is described.

In the above working example 2 the zonde which is inserted into a bore-hole is made up of separate multiple cells, which can apply the pressures independently to the corresponding soil layers via liquid media filled in the cells. The pressure and displacement at the bore-hole wall at each cell are monitored. The zonde is made up of three cells, i.e. a central cell at which the static loading is applied, and top and bottom cells at which the cyclic loading is applied alternatively with one another. By applying the cyclic loading alternatively to the top and bottom cells, the pressure and displacement at the central cell is monitored and examined, which are supposed to undergo some effects of cyclic loading on the top and bottom cells.

However, the effects of cyclic loading imposed by the top and bottom cells are seen eminent to the soil layers located above the top cell and also located beneath the bottom cell. In some cases, there is a possibility that the data which accurately reflect the soil behavior cannot be obtained due to the collapse of the soils located close to the top and bottom cells.

The maintenance of devices in the fields also poses great concern, for instance since the membranes on the zonde need replacement and supplies from time to time.

In the working example 3, it is aimed at offering a testing apparatus, which can monitor the effects of cyclic loading imposed on the soil layers located above the top cell and also located beneath the bottom cell, and which can prevent any irrelevant collapse of soils around the zonde.

It is also intended to offer a testing apparatus which is good for maintenance.

Figure 9:
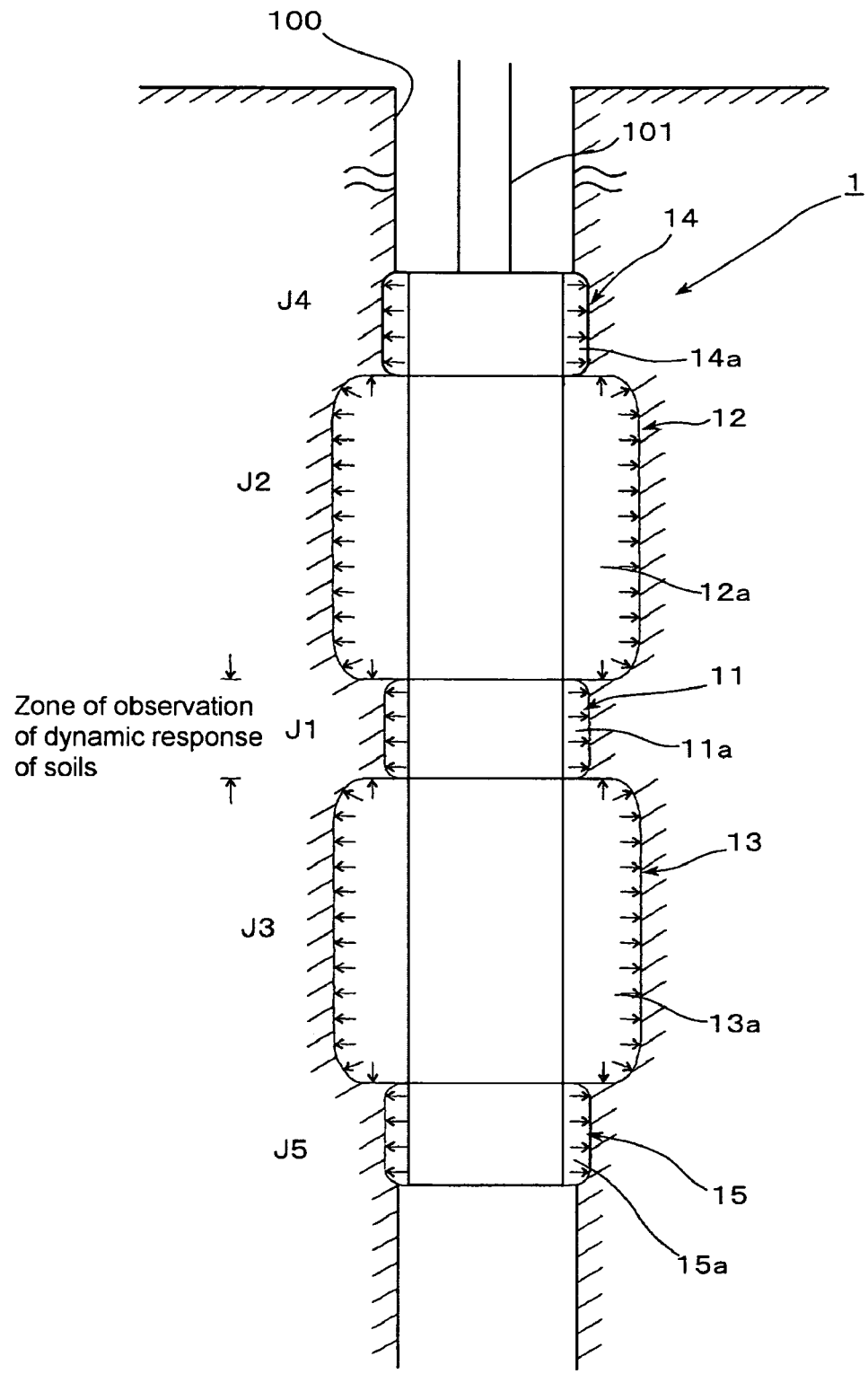
FIG. 9 shows the functions of the monitoring cell of the testing apparatus for liquefaction and dynamic properties of soils using bore-holes, associated with the working example 3.

FIG. 9 shows the schematic illustration of a testing apparatus aimed at exploring in-situ the liquefaction and dynamic properties of soils using bore-holes, with reference to the working example 3 in the present invention.

The monitoring zonde 1, which is lowered down into a bore-hole 100, is composed of a central cell 11 which applies the static loading, top and bottom cells, 12 and 13, which apply the cyclic loading. Herein, the top and bottom cells, 12 and 13, are located above and beneath the central cell 11. The guard cells, 14 and 15, are installed above the top cell 12 and beneath the bottom cell 14, respectively.

The cells of 11, 12, 13, 14 and 15 described above are equipped with the independent pressure rooms, 11*a*, 12*a*, 13*a*, 14*a* and 15*a*. The hydraulic pressures supplied from the pressure rooms, 11*a*, 12*a*, 13*a*, 14*a* and 15*a*, filled with water are supposed to act independently on the soil layers J1, J2, J3, J4 and J5, during which the pressures and displacements at the bore-hole wall are monitored.

Figure 10:
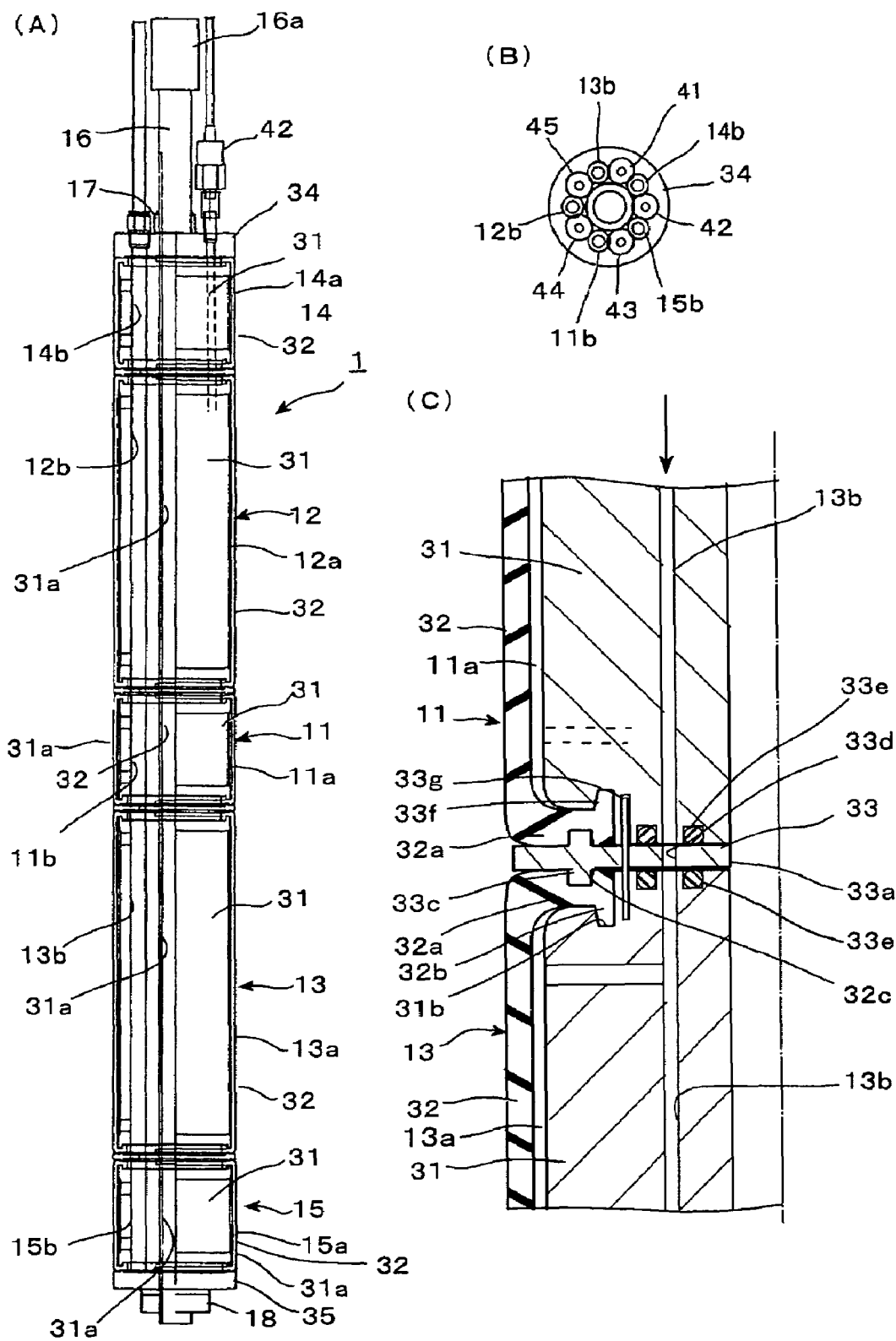
FIG. 10 shows the structural components of the monitoring cell shown in FIG. 9. The cross section and plan view of the entire cell are shown in FIGS. 10 (A) and 10 (B), and the cross section enlarged for the connection parts is shown in FIG. 10 (C).

The cells of 11, 12, 13, 14 and 15 have the same structural components, but with different lengths, as shown in FIG. 10 (A). Each cell has a cylindrically shaped cell body 31, a cylindrical membrane 32 attached to the outer circumference of the cell body and a pressure room of 11*a*, 12*a*, 13*a*, 14*a* and 15*a* filled with a liquid media located between the cell body 31 and the membrane 32. The membrane 32 is cylindrically shaped, and is equipped with the circular projections 32*a* sticking inwards, which are put at the top and bottom ends and connected to the cell body regarding the length of each cell, the total length of the zonde adopted here is 90 cm can be divided into the cells, such as 10 cm each for the central cell, top and bottom guard cells, and 30 cm each for the top and bottom loading cells. The central cell and the top and bottom loading cells can be 15 cm, and the top and bottom guard cells can be as large as 22.5 cm long.

The lengths of the cells can be chosen based on the conditions of loading and types of soils.

The cells of 11, 12, 13, 14 and 15 are designed to be exchangeable with one another. In this working example, the small hole 31a is provided at the center of the cell body 31, and the shaft rod 16 is penetrated through the hole 31a. The upper end of the cells is fixed by the stopper 17 of the shaft rod 16, and the lower end is tightly fixed by the nut 18. The top end of the shaft rod 16 constitutes a connection 16a to fix with a boring rod.

The thin annular ring 33 is provided between the two adjacent cell bodies 31 and other 31.

The circular projection 32a sticking inwards, which is located at the end of the membrane 32 is tightly fixed between the seal plate 33 and the cell body 31, as shown in FIG. 10 (C). The small hole 33a is provided at the center of the circular seal plate 33, through which the shaft rod 16 is penetrated.

At the top and bottom of the sidewall of the circular projection 32a of the membrane 32, the projections, 32b and 32c, are provided, which are connected each with the annular groove 31b located at the end of the cell body 31, and with the circular projection 33c located at the seal plate 33.

The top guard cell 14 is connected with the stopper 16a via the top plate 34, and the bottom guard cell 15 is connected with the nut 17 via the bottom plate 35. On the plates, 34 and 35, the annular groove is provided, which is connected with the projection 33c located at the circular projection 32a of the membrane 32.

Around the cell body 31, the water tubes of 11b, 12b, 13b, 14b and 15b are provided, which are used for filling the pressure rooms of the cells 11, 12, 13, 14 and 15 with water. The pressure tubes of 41a, 42a, 43a, 44a and 45a are provided, which are used for transmitting the pressures generated in the pressure rooms of 11a, 12a, 13a, 14a and 15a into the pressure gauges of 41, 42, 43, 44 and 45. At the top plate 34, the connection ports for the five pressure gauges of 41, 42, 43, 44 and 45, and also for the five water tubes of 11b, 12b, 13b, 14b and 15b. FIG. 10 (A) shows the cross sections, which include the water tube to each cell and the pressure tube to each pressure gauge, and therefore the positions of the cross sections are different at each cell. Each connection port is connected with the pipe to provide a connection with a pump unit. Each pressure gauge is wired electrically. These pressure gauges of 41, 42, 43, 44 and 45 are preferably assembled into one unit.

The water tubes and pressure tubes for the cells located at the lower positions pass through inside the cell bodies located at the upper positions. At the cell body 32 of the guard cell 14 located on top of all the cells, the five water tubes of 11b, 12b, 13b, 14b and 15b, and also the five pressure tubes of 41a, 42a, 43a, 44a and 45a are provided. At the cell body located beneath the guard cell 14, there are 4 water tubes and 4 pressure tubes connected with it. In the same manner, as the cell becomes positioned lower, the number of tubes becomes less one by one, and eventually at the guard cell 15 of the cell body 32 located at the bottom of all the cells, there is only one water tube and one pressure tube connected with it.

In the case of the water tubes and pressure tubes passing through both the upper cell and lower cell, as shown in FIG. 10 (C), the water pipe 13b and the pressure pipe are provided between the upper cell 32 and the lower cell 32, via the connection port 33d located at the seal plate 33. The seal 33e such as an O-ring is provided around the connection port 33d to fill the gap between the seal plate 33 and the upper and lower cells 32. To fix the upper cell and lower cell properly the needle pin 33f is provided at the surface of one of the cells, while the corresponding hole 33g is provided at the surface of the other cell.

Figure 11:
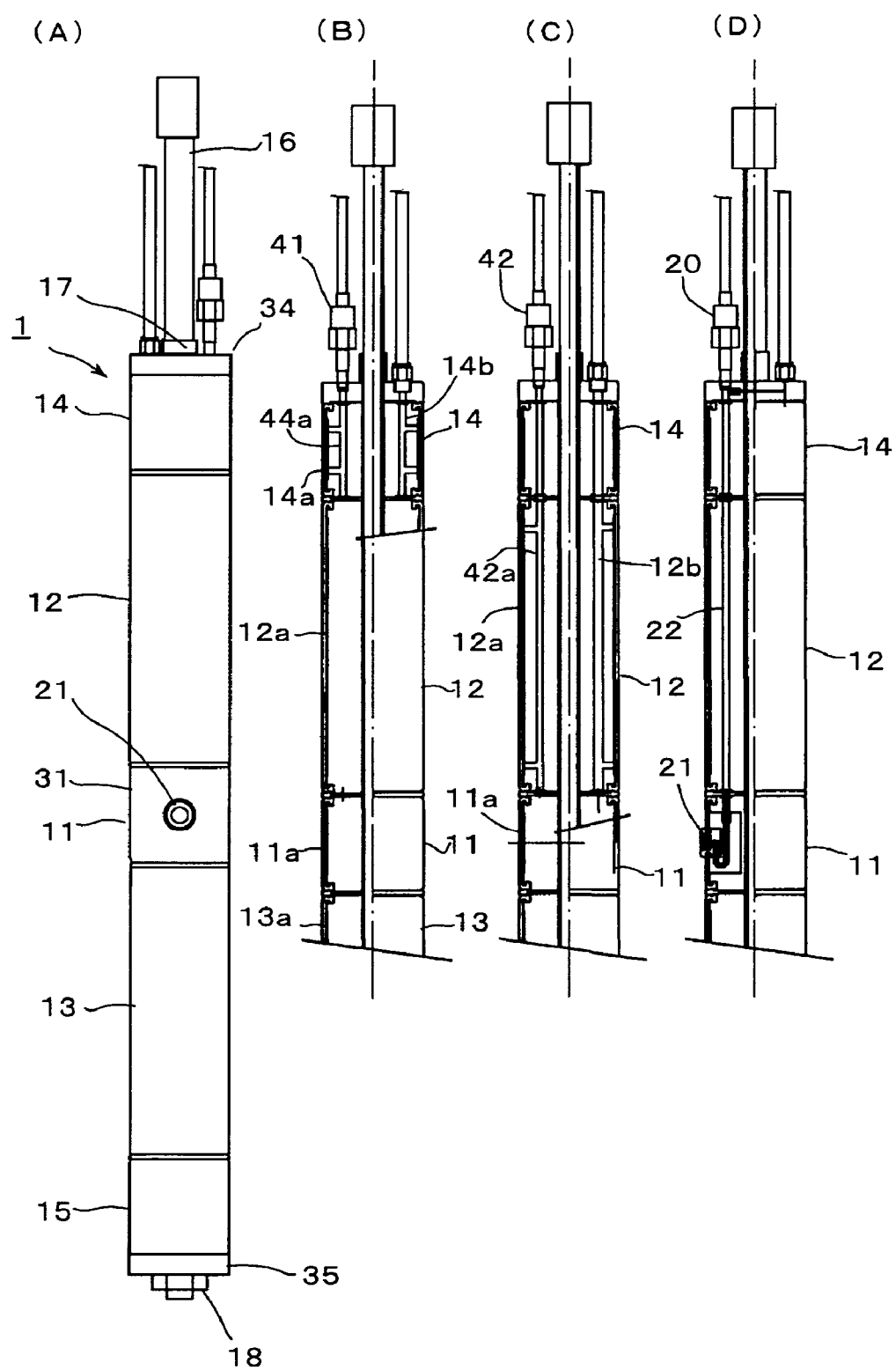
FIG. 11 (A) shows the elevation view of the monitoring cell shown in FIG. 10.

In order to examine the occurrence of liquefaction at the central soil layer J1, to which the central cell 11 applies the loading, as shown in FIGS. 11 (A) and (D), the pressure gauge 20 is provided to monitor the pore water pressure at the soil layer corresponding to the central cell 11.

In the working example, the pore water pressure gauge 20 is located at the top plate 34, and the inlet opening 21 is provided at the surface of the membrane 31 of the central cell 11. The inlet opening 21 and the pore pressure gauge 20 are connected by the pressure tube 22. At the inlet opening 21, the piece of porous stone is embedded to prevent any intrusion of obstacles into the pressure tube. The pore pressure gauge 20 is also preferably assembled together with the pressure gauges of 41 to 45 into one unit.

Regarding the structure of the pore pressure gauge 20, the surface of the sensor itself can be placed at the central cell 11, and the electrical wires can either pass through inside the monitoring cell or it may be monitored by wireless means, or any other means can be adopted.

Figure 12:
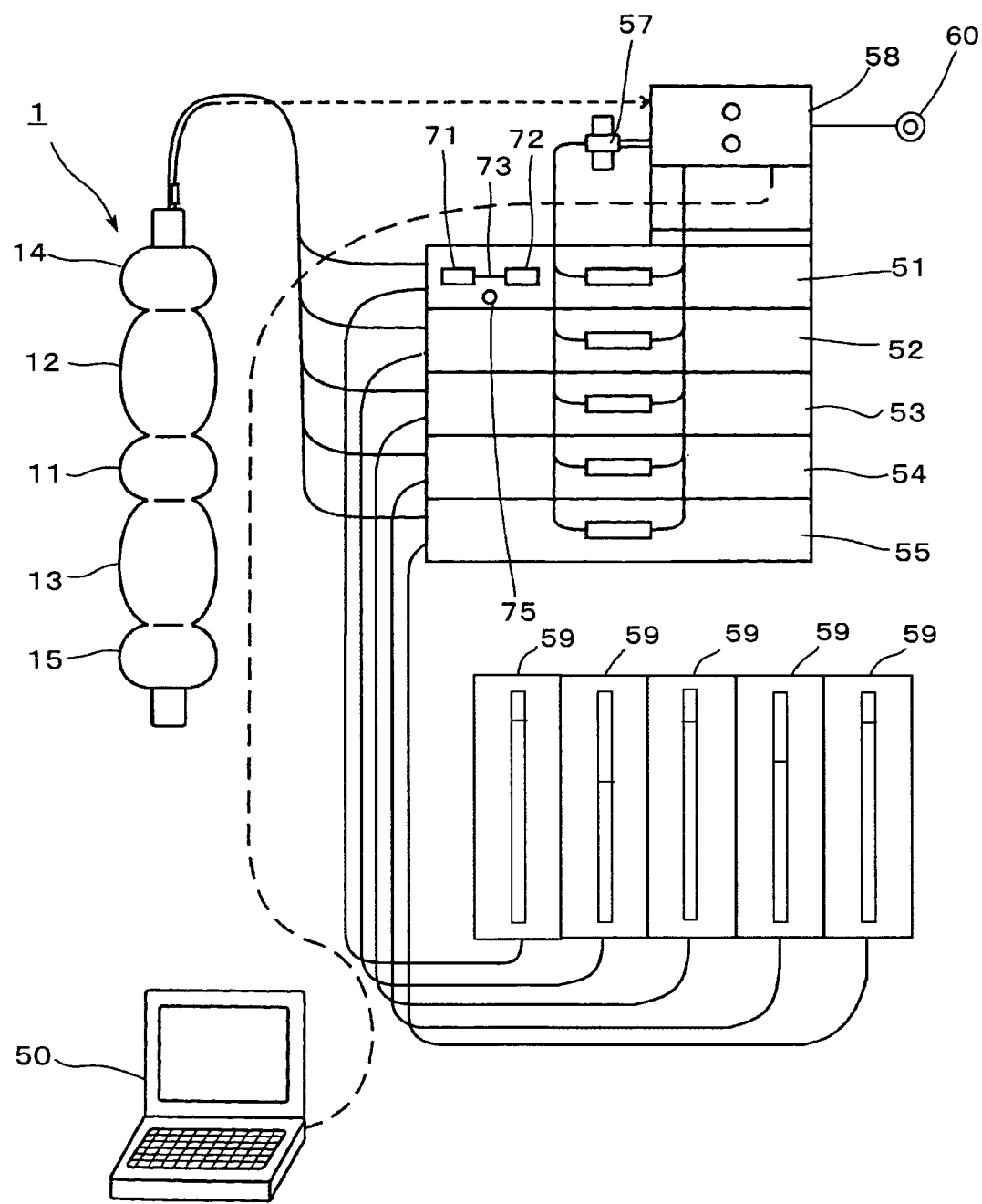
FIG. 12 shows the conceptual illustration of the testing apparatus of the present invention.

FIG. 12 shows one example of the controlling unit for the above monitoring cell.

The controlling unit is composed of several functions. The first one is a series of pumping units of 51, 52, 53, 54 and 55, which are used for transmitting water into the pressure rooms of 11a, 12a, 13a, 14a and 15a of the cells, 11, 12, 13, 14 and 15. The second one is the pressure supplier 60, such as gas cylinders and air compressors, which activate the pumping units of 51, 52, 53, 54 and 55. The third one is the regulator 57, which controls the air pressure coming from the pressure supplier 60. The fourth one is the controlling box 58, which operates the pumping units and the regulator 57. The fifth one is the water tank 59 for the pumping units of 51, 52, 53, 54 and 55. The sixth one is the personal computer 50 with the software for data analyses and graphics, which is wired to the controlling box 58. A series of the pumping units are assembled into one frame with five units on top and the other five units placed in series at the bottom. There can be only one water tank.

Figure 13:
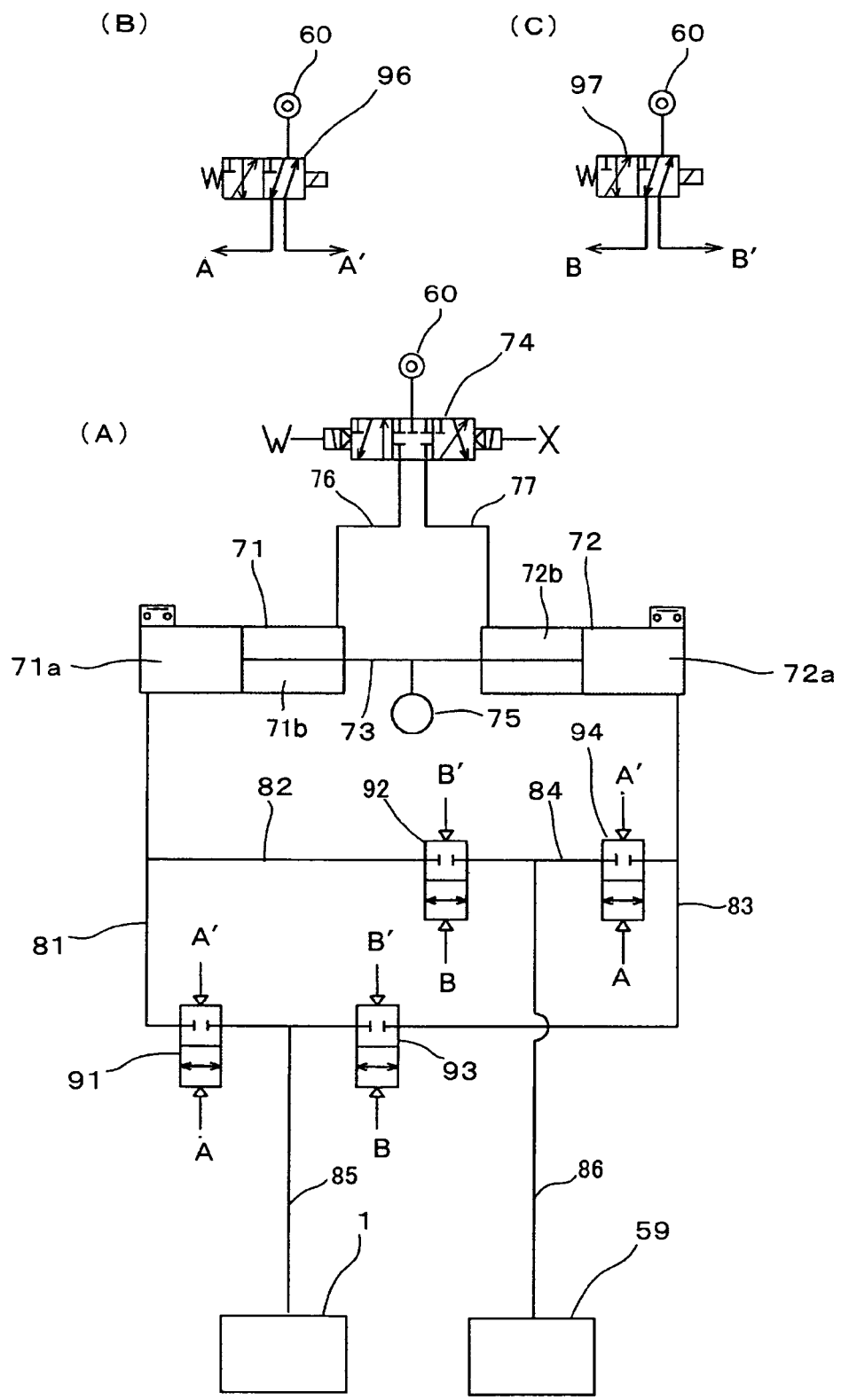
FIG. 13 shows the general layout of the pumping units and associated connections of the testing apparatus shown in FIG. 12.

FIG. 13 shows an example of pumping units. All the pumping units of 51, 52, 53, 54 and 55 have the same structural components, and therefore the structure of the pumping unit 51 is described below.

The pumping unit 51 is composed of a couple of cylinders, 1st cylinder 71 and 2nd cylinder 72, which are inter-connected via the cylinder rod 73, as shown in FIG. 13 (A). There are two rooms in one cylinder, among which the room filled with water is located on the opposite side with respect to the cylinder rod 73. Herein, the water-filled rooms are called 71a and 72a for the cylinders of 71 and 72, respectively. The room 71a of the 1st cylinder 71 is connected to the water tube for the monitoring cell via the 1st water tube 81. Along the 1st water tube 81, the 1st valve 91 is provided. The room 71a is also connected to the water tank 59 via the 2nd water tube 82, which are branched off from the 1st water tube 81. The 2nd water tube is also equipped with the 2nd valve 92.

The room 72a of the 2nd cylinder 72 is connected to the water tube corresponding to the monitoring cell 1 via the 3rd water tube 83. Along the 3rd water tube 83, the 3rd valve 93 is provided. The room 72a is connected to the water tank 59 via the 4th water tube which is branched off from the 3rd water tube 83. Along the 4th water tube 84, the 4th valve 94 is provided.

The 1st water tube 81 and the 3rd water tube 83 are designed to join together at the downstream of the 1st valve 91 and the 3rd valve 93, and are then connected to the monitoring cell via the united line of the 1st and 3rd water tubes 85. The 2nd water tube 82 and the 4th water tube 84 are designed to join together at the downstream of the 2nd valve 92 and the 4th valve 94, and are then connected to the water tank 59 via the united line of the 2nd and 4th water tubes 86.

The 1st valve 91 and the 3rd valve 93 are activated by the air pressure supplied from the air pressure supplier 60. The air pressure is controlled by the electromagnetic valve 96 used for the control of the 1st valve, as shown FIG. 13 (B). The 2nd valve 92 and the 4th valve 94 are activated by the air pressure, which are controlled by the electromagnetic valve 97 used for the control of the 2nd valve, as shown in FIG. 13 (C).

Located at the sides of the rods in the 1st cylinder 71 and 2nd cylinder 72 are the air pressure rooms of 71*b* and 72*b*. The air pressures are selectively introduced into the air pressure rooms of 71*b* and 72*b* via the electromagnetic valve 74 used for activating cylinders, 1st air tube 76 and 2nd air tube 77. This electromagnetic valve is the control valve with 5 ports and 3 positioning controls. The 3 positioning controls correspond to the pressure-supplying position for the 1st cylinder, the neutral position, and the pressure-supplying position for the 2nd cylinder.

The pressure-supplying position for the 1st cylinder is designed to supply the air pressure into the air room 71*b* of the 1st cylinder 71, and to release the air pressure in the air room 72*b* of the 2nd cylinder 72. The pressure-supplying position for the 2nd cylinder is designed to supply the air pressure into the air room 72*b* of the 2nd cylinder, and to release the air pressure in the air room 71*b* of the 1st cylinder 71.

In the case of increasing the pressure in the pressure room of the monitoring cell 1, the electromagnetic valve 74 for activating cylinders is switched into the pressure-supplying position for the 1st cylinder. In addition, the electromagnetic valve 96 used for the control of the 1st valve is switched on, while the electromagnetic valve 96 used for the control of the 2nd valve is switched off. Moreover, the 1st valve 91 and the 4th valve 94 are opened, while the 2nd valve 92 and the 3rd valve 93 are closed. From the pressure supplying unit such as an air compressor, the air pressure is supplied into the air room 71*b* of the 1st cylinder 71 via the 1st airtube 76, and the water-filled room 71*a* of the 1st cylinder 71 is compressed. The 2nd and 3rd valves of 92 and 93 are closed, and therefore, the liquid medium of water in the water-filled room 71*a* of the 1st cylinder 71 is introduced into the pressure room of the monitoring cell 1 via the united line of the 1st and 3rd water tubes R5, and supplies the pressure. Consequently, the other water-filled room 72*a* of the 2nd cylinder 72 is subjected to volume expansion and there are, the liquid medium of water in the water tank 59 is allowed to flow into the room 72*a* via the united line of the 2nd and 4th water tubes 86 and also the 4th water tube 84.

Then, the electromagnetic valve 74 for activating cylinders is switched into the 2 pressure supplying position for the 2nd cylinder. In addition, the electromagnetic valve 96 used for the control of the 1st valve is switched off, while the electromagnetic valve 96 used for the control of the 2nd valve is switched on. Moreover, the 1st valve 91 and the 4th valve 94 are closed, while the 2nd valve 92 and the 3rd valve 93 are opened. From the pressure supplying unit 60 such as an air compressor, the air pressure is supplied into the air room 72*b* of the 2nd cylinder 72 via the 2nd air tube 77, and the water-filled room 72*a* of the 2nd cylinder 72 is compressed. The 1st and 4th valves of 91 and 94 are closed, and therefore, the liquid medium of water in the water-filled room 72*a* of the 2nd cylinder 72 is introduced into the pressure room of the monitoring cell 1 via the 3rd water tube and also the united line of the 1st and 3rd water tubes 85, and supplies the pressure while the other water-filled room 71*a* of the 1st cylinder 71 is subjected to volume expansion, and therefore, the liquid medium of water in the water tank 59 is then allowed into the room 71*a* via the united line of the 2nd and 4th water tubes 86 and also the 2nd water tube 82.

By repeating the same operations, the pressure in the monitoring cell is gradually increased.

In the case of reducing the pressure in the pressure room of the monitoring cell 1, the electromagnetic valve 74 for activating cylinders is switched into the pressure-supplying position for the 2nd cylinder 72. The cylinder rod 73 is then moved to the right direction in the diagram.

The liquid medium of water in the monitoring cell 1 is then forced to move into the water-filled room of the 1st cylinder 71, and the liquid medium of water in the water-filled room of the 2nd cylinder 72 returns back to the water tank 59.

In the case of reducing the pressure in the pressure room of the monitoring cell 1, the electromagnetic valve 74 for activating cylinders is switched into the pressure-supplying position for the 2nd cylinder. In addition, the electromagnetic valve 96 used for the control of the 1st valve is switched on, while the electromagnetic valve 96 used for the control of the 2nd valve is switched off. Moreover, the 1st valve 91 and the 4th valve 94 are opened, while the 2nd valve 92 and the 3rd valve 93 are closed. From the pressure supplying unit 60 such as an air compressor, the air pressure is supplied into the air room 72*b* of the 2nd cylinder 72 via the 2nd air tube 77, and the water-filled room 72*a* of the 2nd cylinder 72 is compressed. The 2nd and 3rd valves of 92 and 93 are closed, and therefore, the liquid medium of water in the water filled room 72*a* of the 2nd cylinder 72 returns back into the water tank 59 via the 4th water tube and also the united line of the 2nd and 4th water tubes 86.

Consequently the other water-filled room 71*a* of the 1st cylinder 71 is subjected to volume expansion, and therefore, the liquid medium of water in the pressure room of the monitoring cell 1 is allowed to flow into the room 71*a* via the united line of the 1st and 3rd water tubes 85 and also the 1st water tube 81.

The electromagnetic valve 74 for activating cylinders is then switched into the pressure-supplying position for the 1st cylinder. In addition, the electromagnetic valve 96 used for the control of the 1st valve is switched off, while the electromagnetic valve 96 used for the control of the 2nd valve is switched on. Moreover, the 1st valve 91 and the 4th valve 94 are closed, while the 2nd valve 92 and the 3rd valve 93 are opened. From the pressure supplying unit 60 such as an air compressor, the air pressure is supplied into the air room 71*b* of the 1st cylinder 71 via the 1st air tube 76, and the air room 71*a* of the 1st cylinder 71 is compressed. The 1st and 4th valves of 91 and 94 are closed, and therefore, the liquid medium of water in the water-filled room 71*a* of the 1st cylinder 71 is let flow back into the water tank 59 via the 2nd water tube and also the united line of the 2nd and 4th water tubes 86. Consequently, the other water-filled room 72*a* of the 2nd cylinder 72 is subjected to volume expansion, and therefore, the liquid medium of water in the pressure room of the monitoring cell 1 is now allowed into the room 72*a* via the united line of the 1st and 3rd water tubes 85 and also the 3rd water tube 83.

By repeating the same operations, the pressure in the monitoring cell is gradually reduced.

Each pumping unit is equally equipped with the displacement sensor 75 to monitor the amplitude (stroke) of the movement of the rod of the cylinder. From the outputs of this displacement sensor 75, the volume of the water flowing in and out of the monitoring cell 1 is calculated. During the process of increasing the pressure, the volume of the water flowing in and out of the monitoring cell is calculated by adding the amplitudes of the movements of the 1st cylinder 71 and 2nd cylinder 72. During the process of reducing the pressure, it is calculated by subtracting the amplitude of the movement of the 1st cylinder 71 from that of the 2nd cylinder 72. The radial displacements of the bore-hole wall are then calculated from the change in the volume of the water thus obtained.

The control of the pressure increase and decrease in the pumping unit is carried out in the following manner. The expected time history of the pressure change is produced as reference data. The outputs from the pressure gauge are monitored and transmitted back as a feedback to the electromagnetic valves of 74, 96 and 97, and the open/close operations of these valves are controlled to follow accurately the expected time history of the pressure change.

The pressure change is designed to fluctuate periodically up and down with respect to the reference pressure level set up at each base pressure level, while the reference pressure level is increased as the cycles of the pressure change proceed. The waveform can be taken in the form of a sinusoidal shape, or in the form of a rectangular shape, or in the forms of any other shapes, depending on the conditions of the tests. The monitored data of the pressure gauges are transmitted to the personal computer as feedback. Upon receiving such feedback, the personal computer serves as the transmitter of the digital signals for the open/close operations of the electromagnetic valves of 74, 96 and 97. The pressure changes are controlled to accurately follow the pre-determined time history. The operation of control particularly depends on whether it is in the process of increasing the pressure or reducing the pressure.

The feedback can be conducted not only with respect to the amplitude of the pressure, but also with respect to the displacement (stroke) of the movement of the cylinder rod.

Figure 16:
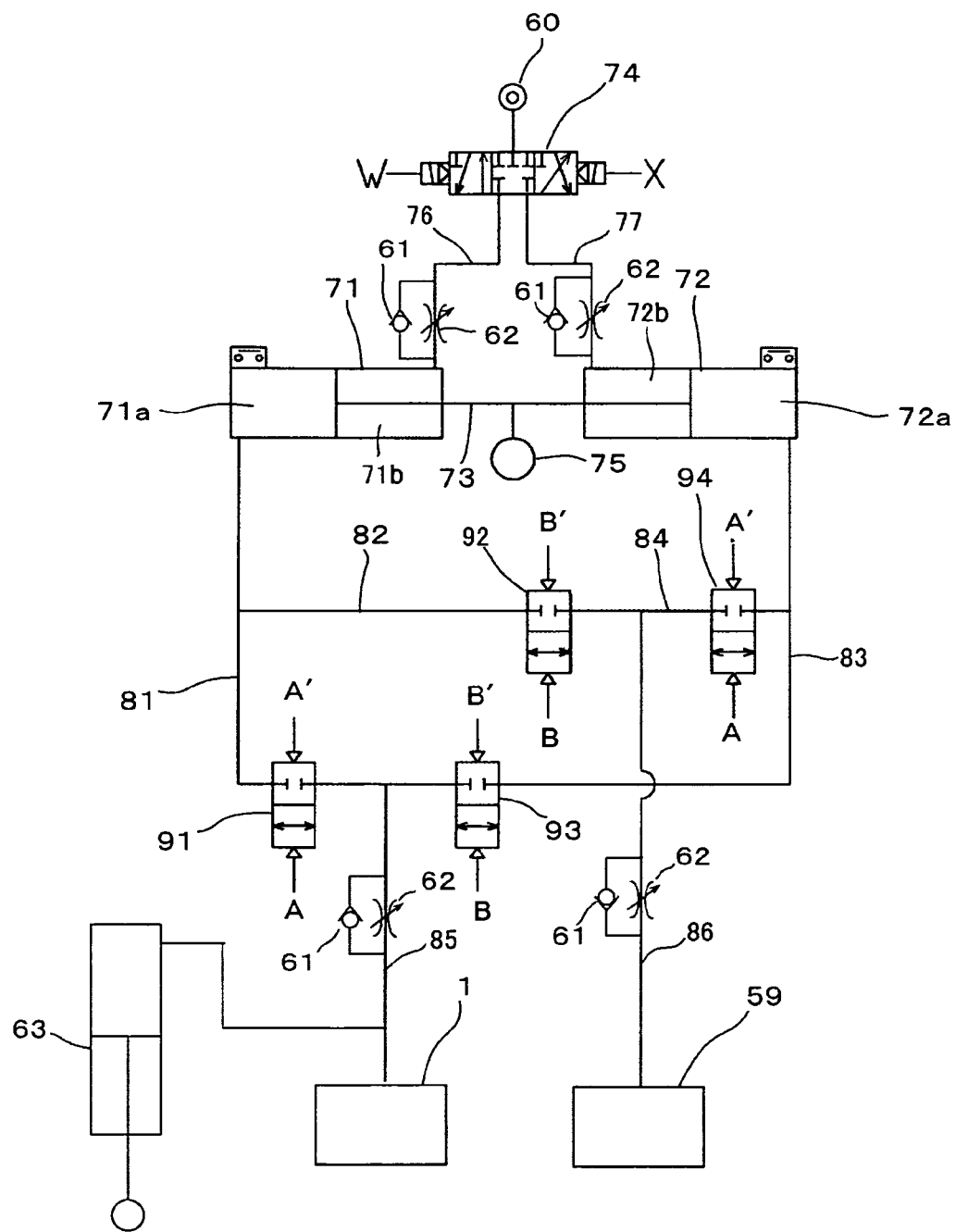
FIG. 16 shows the extended version of the layout shown in FIG. 13.

The air bubbles due to cavitation might be generated and the response of the pressure control might be worsened when the pressure is reduced rapidly. Therefore, in order to control the speed (flow rate), as shown in FIG. 16, the flow-rate control valve 62 equipped with the function of back-flow prevention 61 can be installed along the united line of the 1st and 3rd water tubes 85 and the united line of the 2nd and 4th water tubes 86. The valve for the back-flow prevention 61 and the flow-rate control valve 62 are installed in parallel.

The valve for the back-flow prevention 61, installed along the united line of the 1st and 3rd water tubes 85 connected with the monitoring cell 1, allows the inflow towards the monitoring cell, but prevents the outflow from the monitoring cell. Therefore, the flow rate is controlled during the outflow from the cell, while the flow smoothly takes place during the inflow towards the cell, with a help of the valve for the back-flow prevention, which serves as a bypass line on behalf of the flow-rate control valve.

The flow rate control valve 62 equipped with the function of back-flow prevention 61 can be installed along the 1st air tube 76 and 2nd air tube 77, which are located between the electromagnetic valve 74 for activating cylinders and the 1st cylinder 71 and 2nd cylinder 72. The valve for the back-flow prevention 61 might be installed in such a manner that allows the inflow towards the air rooms of 71b and 72b, but prevents the outflow from these rooms.

In this working example, the 1st cylinder 71 and 2nd cylinder 72 are activated to produce a given pressure change during cyclic loading. However, as shown in FIG. 16, the alternative method is also possible by connecting the cylinder for cyclic loading 63 with the united line of the 1st and 3rd water tubes 85. After increasing the pressure up to a given point using the 1st cylinder 71 and 2nd cylinder 72, the cyclic loading can be conducted by making the cylinder 63 for cyclic loading move back and forth periodically. It is also possible to organize the system, in which the back and forth movement of this cylinder 63 can be applied mechanically instead of hydraulically.

The testing procedure is described in detail below.

The bore-hole 100 is produced down to a given depth of testing. The monitoring cell 1 is lowered down to a given depth into the bore-hole 100 using the boring rod 100. First, the pressures are supplied into the pressure rooms of 11a, 12a, 13a, 14a and 15a, which are belonging to the central cell 11, top and bottom cells of 12 and 13, and the top and bottom guard cells of 14 and 15, until the membranes of all the cell are intimately attached to the bore-hole wall.

The pressures are equally increased in the central cell 11, and the top and bottom guard cells of 14 and 15.

The cyclic changes of the pressures are applied to the liquid media of water in the pressure rooms of 12a and 13a belonging to the top cell 12 and bottom cell 13. The outputs from the pressure gauges of 41, 42, 43, 44 and 45, and also from the now-rate sensors 75 of all the pumping units are read off and stored into the personal computer 50. The pressures in the pressure rooms and the radial displacements at the bore-hole wall are all displayed on the PC monitor. The output from the pore water pressure gauge 20 installed at the central cell 11 is also read off and stored into the personal computer 50.

From the cyclic pressure-displacement relations obtained by applying the cyclic pressures to the top and bottom cells of 12 and 13 with a frequency of 0.1 to 1 Hz, the dynamic deformation and strength characteristics of soils can be examined.

Figure 14:
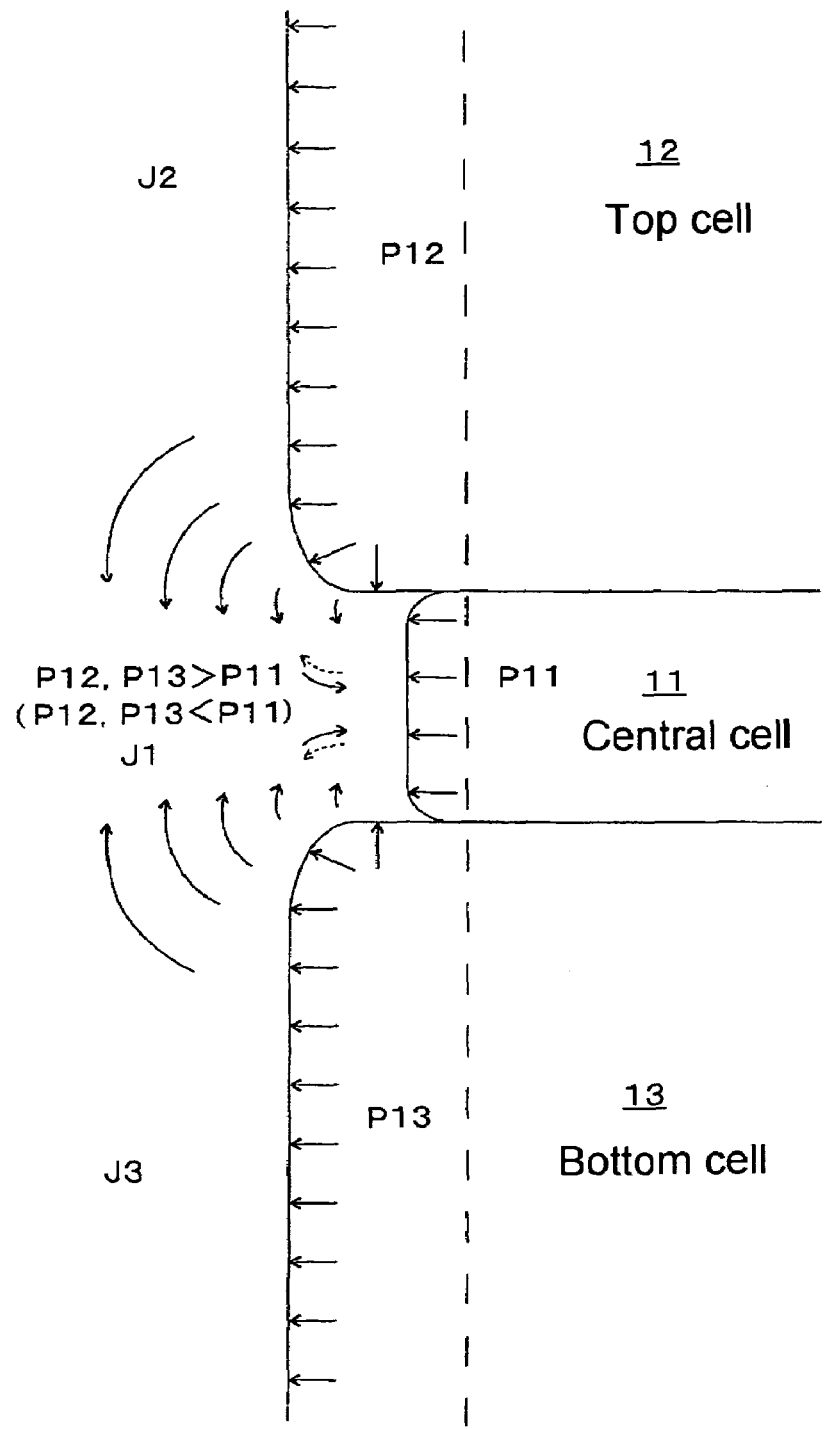
FIG. 14 shows the schematic illustration of loading against a bore-hole wall during the tests.

By applying the cyclic pressures to the top and bottom cells of 12 and 13, as shown in FIG. 14, three levels of the pressures, P11, P12 and P13, are applied at the side wall of the central cell 11. When the levels of the pressures P12 and P13 become larger than P11, the state of yield and ultimately the state of failure begins to prevail within the soil layer J1, and the phenomenon of the central cell 11 being pushed back inwards by the collapsing soils is observed. Depending on the conditions of soils, the level of the pressure P11 becomes less than P12 and P13, and the phenomenon of the central cell being pulled off outwards is observed as indicated by a dashed line. Therefore, it is possible to examine the dynamic characteristics of the soil layer J1, by monitoring the displacements of the central cell 11 and distinguishing whether the central cell is pushed inwards or pulled outwards. In case of sandy soils, these phenomena associated with the behavior of the central cell can be identified as the collapse of the soils and ultimately soil liquefaction. In the testing apparatus adopted in the present invention, the behavior of the pore water pressures at the soil layer J1 can be monitored directly using the pore water pressure gauge 20. Therefore, it is possible to offer the useful data associated with soil liquefaction. For instance, the correlation between the pore water pressure behavior and the pressure-displacement relations can be examined, especially at the collapsing state where the displacement rapidly increases.

Figure 15:
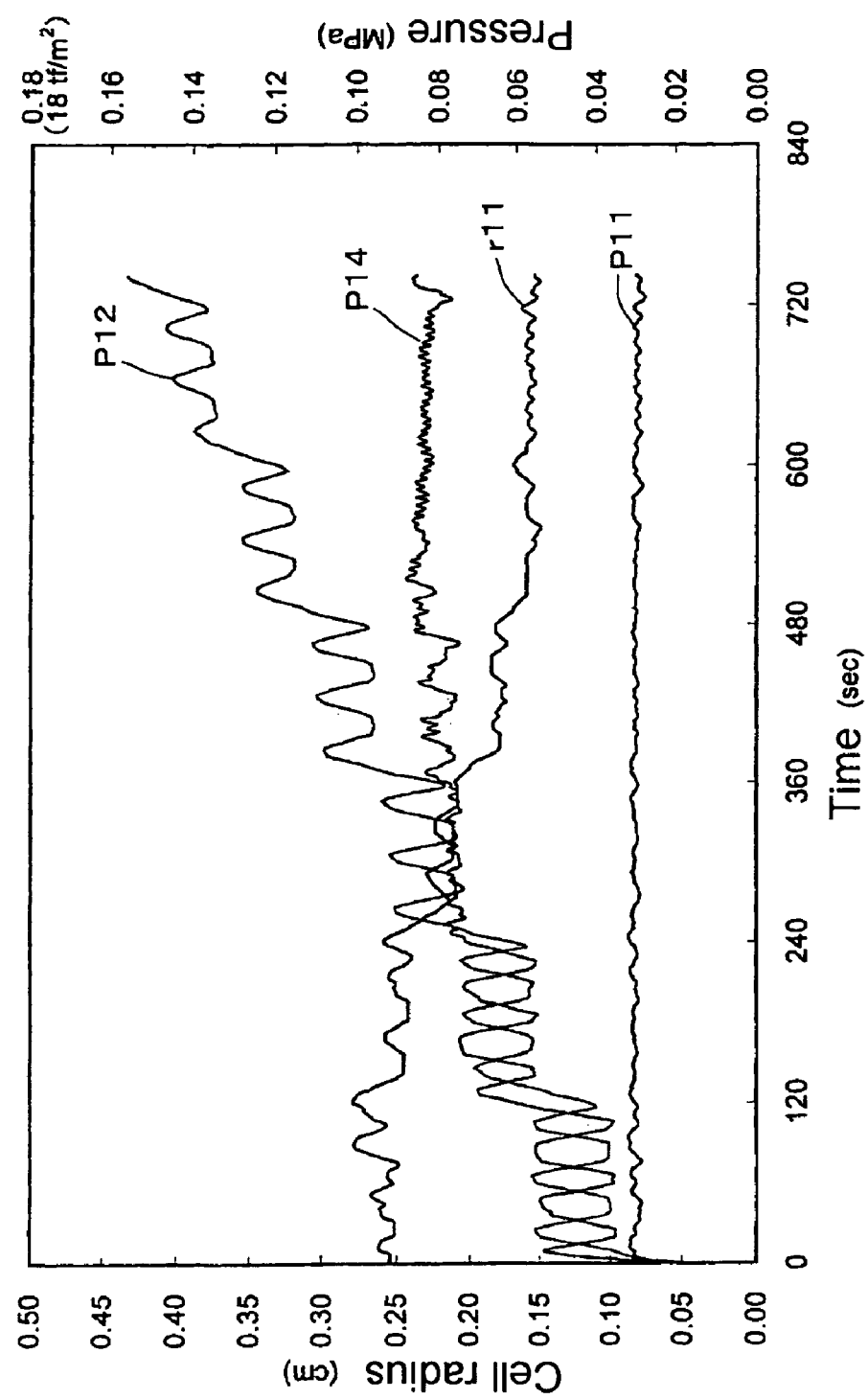
FIG. 15 shows the diagram of the test results.

FIG. 15 shows the real data obtained by this testing apparatus. It is seen that the negative displacement occurs at around 240 seconds, and it is considered that the collapse begins at this stage.

By conducting the static loading tests after the cyclic loading, the strength reduction due to fatigue can be estimated in case of clayey soils, while the residual strength during liquefaction can be estimated in case of sandy soils.

The behavior of the displacements at the top and bottom guard cells of 14 and 15 can also be monitored and recorded. By comparing such data with the data of the central cell 11, the verification, analysis and interpretation of the data becomes more rational.

Figure 17:
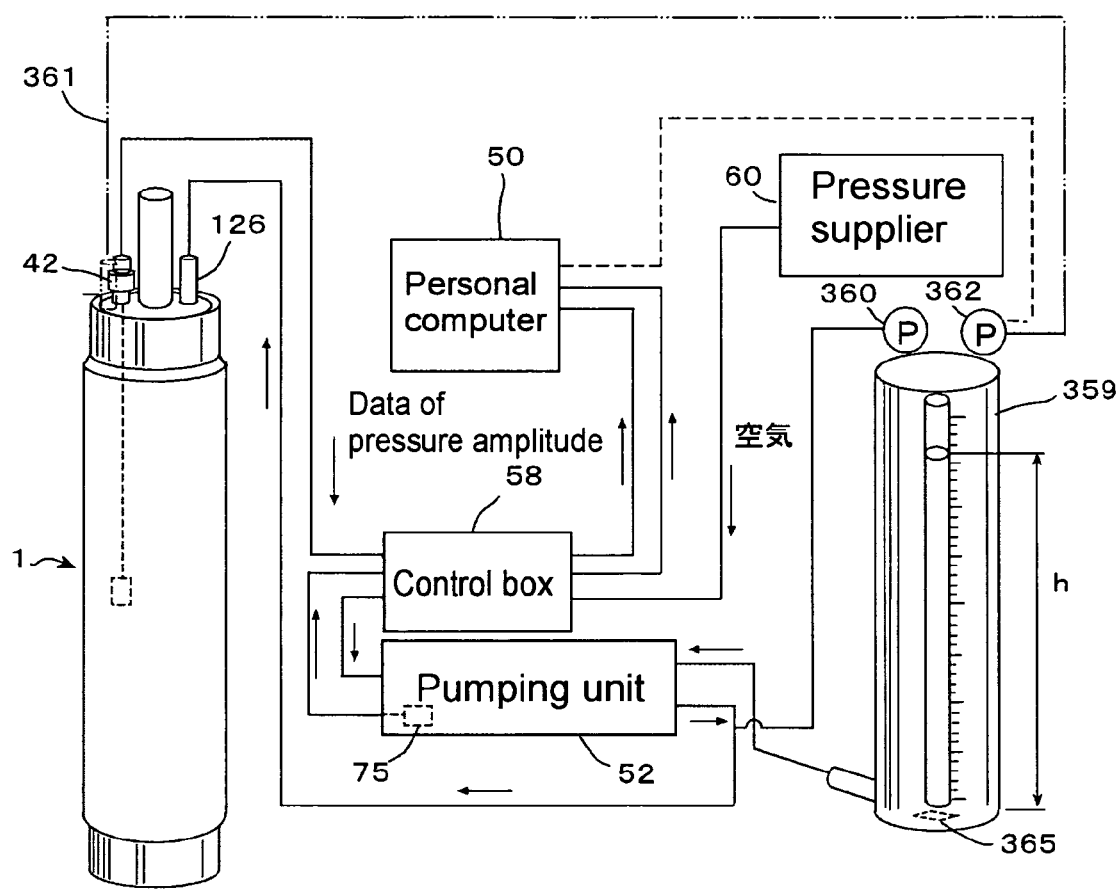
FIG. 17 shows the conceptual illustration of the testing apparatus for the extended version of the working example 3 of the present invention.

FIG. 17 shows an extended version of the working example 3.

The basic structural components are the same as in the working example 3. So, the components that are different from the working example 3 are described below. The identical components are coded with the same symbols.

In this example, the circular water tank 359 is equipped with the scale along its side. So, the volume of the water flowing in and out of the monitoring cell 1 can be measured by the manual reading of the scale as well as by the displacement (stroke) sensor 75. By monitoring the water level of the water tank, the operator can have some direct information regarding the displacements of the bore-hole wall. The reliability of data can also be improved by installing the monitoring sensor 365 for the water level, and storing the data in the personal computer, and then comparing the data of the volume of the water which are calibrated by the water level against those calibrated by the displacement (stroke) sensor 75. In this example, the monitoring sensor 356 of the water level is a pressure transducer, and is installed at the bottom of the water tank 359. The hydrostatic pressure gained from the pressure transducer is calibrated to a depth of water, from which the change in the water level is calculated. It is also possible to adopt any other means for the water level measurement, such as a floating buoy and other available sensors.

The pressure gauge equipped with a scale 360 can be installed along the tube between the pumping unit and the monitoring cell. By locating the pressure gauge above the water tank 359, the change of the pressure supplied from the pumping unit and the water level in the water tank 59 can be manually monitored. By this means, it is possible to acquire some direct information with respect to the pressure supplied and the displacements at the bore-hole wall (radial deformation of the membrane of the monitoring cell 1). The pressure gauge 360 can be an analogue-type or a digital-type.

The data of the pressure thus obtained from the pressure gauge 360 are transmitted into the personal computer 50. By comparing such data with the pressures measured at the pressure rooms in the cells, the influence of the flexibility of the tubes can be examined, and thus the reliability of data can be improved.

It is also possible to install the pressure gauge equipped with a scale for the pressure rooms of the monitoring cell 1 in the following manner. The tube 361 is extended up to the ground surface from each of the pressure rooms of the monitoring cell located in the bore-hole. The pressure gauge 362 can be installed along this extension tube 361, and put above the water tank 359 along side the pressure gauge 360 measuring the pressure supplied from the pumping unit. By this means, it can be monitored directly with a scale, together with the pressure supplied from the pumping unit and the water level of the tank 359. The data of the pressures monitored by the pressure gauge 362 is also transmitted to the personal computer 50, and, therefore, the reliability of data can also be improved by comparing it with the data of the pressure originally supplied from the pumping unit.

Using the testing apparatus shown in this working example 3, it is also possible to conduct conventional monotonic pressure meter tests by applying the static loading via the top and bottom cells of 12 and 13. In this case, the soil layer around the central cell 11 is subjected to the static compression from both of the top and bottom cells, 12 and 13. So, the useful information can be deducted from the pressure-displacement behavior at the central cell during such tests. In this working example 3, the control of cyclic loading is conducted using pumping units. However, it is also possible to control the cyclic loading using servo-valves.

Instead of the monitoring cells equipped with multiple pressure rooms adopted in the invention, it is also possible to connect a conventional type of pressuremeters equipped with only one pressure room with the driving and controlling unit adopted in the present invention. By this means, it becomes possible to conduct conventional monotonic pressuremeter tests in a more controlled manner, as it is used to be conducted manually. Full automatic pressuremeter test equipment is available, but the replacement of the whole system is not cost-effective. Instead, by adopting the testing apparatus in the present invention, the conventional pressuremeter test equipment can also be recycled, and the full automatic conventional tests can be conducted.

INDUSTRIAL APPLICABILITY

The present invention allows in-situ examination of dynamic strength and deformation characteristics of soils during cyclic loading without any soil sampling. In addition, it is possible to conduct tests on loose sand deposits, gravel-containing soil deposits, soil deposits involving large-sized grains such as sandy gravels, weathered rocks and soft rocks, which are difficult to soil sample, and therefore its utility extends to such soil deposits. It is also time and cost-effective, compared with the conventional sampling and laboratory tests.

It is especially noteworthy that by applying the cyclic loading alternatively to the multiple locations along the bore-hole axis, the cyclic shear stress is induced at the boundaries of the loaded areas. So, the characteristics of soils against cyclic shear loading as well as against cyclic compressional loading can be examined. Soil liquefaction is associated with shear loading, so the assessment of liquefaction occurrence can also be examined. When the collapse of soils occurs, the liquefaction might propagate into the compressionally loaded areas, and the displacement might change greatly.

EXPLANATIONS OF LETTERS OR NUMERALS

201: Membrane zonde (monitoring cell)
202: Water tank
203: Water (liquid medium)
204: Pressure supplier
205: Pressure valve
206: Connection tube
207: Personal computer
209: Torque generation unit
210: Monitoring unit for displacement
211: Device for generating shear loading
212: Monitoring unit for displacement
100: Boring hole
111, 112, 113: 1st, 2nd, 3rd cells
121, 122, 123: 1st, 2nd, 3rd pressure controlling device
114: Cell body
115: Membrane
116: Connection parts
120A: Gas cylinder
120B: Gas tank 121C, 123C: Hydraulic cylinders
121D, 123D: Valves
121E, 123E: Valves
122C: Water tank
122D: Pressure valve
J1: Top soil layer
J2: Central soil layer
J3: Bottom soil layer
150: Pore water pressure gauge
100: Bore-hole
1: Monitoring cell
11: Central cell
12: Top cell
13: Bottom cell
14: Top guard cell
15: Bottom guard cell
11a, 12a, 13a, 14a, 15a: Pressure rooms
J1, J2, J3, J4, J5: Soil layers
31: Cell body
32: Membrane
33: Seal plate
34: Top plate

The invention claimed is:

1. An in-situ testing method for the evaluation of liquefaction and dynamic characteristics of soils using bore-holes, comprising the steps of applying cyclic loading alternatively to multiple zones located along the bore-hole axis to thereby apply cyclically alternating shear loading at a central soil layer located between two adjacent loaded zones, and monitoring displacements of a bore-hole wall during application of the cyclic loading imposed on the bore-hole wall at a given testing soil layer.

2. The in-situ testing method according to claim 1, which is aimed at deriving strength by applying static loading to the central soil layer after the cyclic loading imposed on the same soil layer.

3. An in-situ testing method for the evaluation of liquefaction and dynamic characteristics of soils using bore-holes, which is aimed at inferring dynamic characteristics of soils from relations among amplitudes of cyclic loading, number of cycles and displacements, during the conduct of application of cyclic loading imposed alternatively on a single zone located along the bore-hole axis to thereby apply cyclically alternating shear loading at a central soil layer located between two adjacent loaded zones, wherein displacements of a bore-hole wall during application of the cyclic loading imposed on the bore-hole wall are monitored at a given testing soil layer.

4. The in-situ testing method according to claim 3, wherein the cyclic loading uses one or combinations of three loading types: (i) compressional loading imposed orthogonal to the bore-hole axis, (ii) torsional loading imposed around the bore-hole axis, and (iii) shear loading imposed parallel to the bore-hole axis.

5. An in-situ testing apparatus for the evaluation of liquefaction and dynamic characteristics of soils using bore-holes, comprising a monitoring zonde that is lowered down into the bore-hole and applies pressure to the bore-hole wall via a pressure-transmitting medium, a pressure controlling unit that changes the pressure carried by the medium in the monitoring zonde periodically, and a monitoring unit for monitoring displacement of the bore-hole wall wherein the monitoring zonde comprises multiple cells located along the bore-hole axis that applies the pressure to the bore-hole wall, and the pressure controlling unit applies the cyclic pressure alternatively to these multiple cells.

6. The in-situ testing apparatus according to claim 5, wherein the pressure controlling unit applies the cyclic pressures alternatively to the top and bottom cells and can apply the static pressure to the central cell.

7. An in-situ testing apparatus for the evaluation of liquefaction and dynamic characteristics of soils using bore-holes comprising a monitoring zonde that is lowered down into the bore-hole and applies pressure to the bore-hole wall via a pressure-transmitting medium, a pressure controlling unit that changes the pressure carried by the medium in the monitoring zonde periodically, a monitoring unit for monitoring displacement of the bore-hole wall, a torque generating unit that applies cyclic loading around the bore-hole axis with the monitoring cell intimately attached to the bore-hole wall, and a monitoring unit for monitoring rotational displacements generated by the torsional cyclic loading.

8. The in-situ testing method according to claim 7, further comprising a shear load-generating unit that applies cyclic loading parallel to the bore-hole axis with the monitoring cell intimately attached to the bore-hole wall, and a monitoring unit for monitoring shear (axial) displacements generated by the cyclic shear loading.

9. An in-situ testing apparatus for the evaluation of liquefaction and dynamic characteristics of soils using bore-holes, comprising a monitoring zonde lowered down into the bore-hole, the monitoring zonde comprising multiple cells that have independent pressure rooms, and each independent cell is designed to apply a loading to the corresponding soil layer by controlling the pressure carried by a liquid medium in the pressure room, wherein a central cell of the multiple cells applies a static loading and top and bottom cells apply cyclic loading to corresponding soil layers, said monitoring zonde further comprising top and bottom guard cells provided on top of all the cells and beneath all of the cells, respectively.

10. The in-situ testing apparatus according to claim 9, further comprising a pore water pressure gauge located at the central cell of the monitoring zonde.

11. The in-situ testing apparatus according to claim 10, further comprising pore water pressure gauge that possesses a sensor unit on the surface of the inflatable membrane of the central cell.

12. The in-situ testing apparatus according to claim 9, further comprising a cylinder that generates pressure carried by the liquid medium in the pressure room, a monitoring unit for measuring movement of a rod connected to the cylinder, and a unit for deriving displacement of the bore-hole wall from the measurement of the movement of the cylinder rod.

13. An in-situ testing apparatus for the evaluation of liquefaction and dynamic characteristics of soils using bore-holes, comprising a monitoring zonde lowered down into the bore-hole, said monitoring zonde comprising multiple cells that have independent pressure rooms, with each independent cell being designed to apply loading to a corresponding soil layer by controlling the pressure carried by a liquid medium in the pressure room, and each cell is independent and connections between the cells are exchangeable.

14. The in-situ testing apparatus according to claim 13, wherein each cell is composed of a cell body itself, a cylindrical membrane attached to the circumference of the cell body, and a pressure room filled with a liquid medium located between the cell body and the membrane.

15. The in-situ testing apparatus according to claim 14, further comprising seal plates inserted between the cells, so that the membranes of the adjacent cells can be intimately connected with each other.

* * * * *